(12) United States Patent
Papadopoulos et al.

(10) Patent No.: US 7,056,694 B1
(45) Date of Patent: Jun. 6, 2006

(54) DNA ENCODING PERIPHERAL-TYPE BENZODIAZIPINE RECEPTOR ASSOCIATED PROTEIN 7 AND APPLICATIONS OR METHODS OF USE

(75) Inventors: Vassilios Papadopoulos, North Potomac, MD (US); Hua Li, North Potomac, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/762,594

(22) PCT Filed: Aug. 11, 1999

(86) PCT No.: PCT/US99/18507

§ 371 (c)(1),
(2), (4) Date: Jun. 22, 2001

(87) PCT Pub. No.: WO00/09549

PCT Pub. Date: Feb. 24, 2000

Related U.S. Application Data

(60) Provisional application No. 60/096,048, filed on Aug. 11, 1998.

(51) Int. Cl.
*C07H 21/04* (2006.01)
*C12N 1/20* (2006.01)
*C12N 15/09* (2006.01)
*C12N 5/00* (2006.01)
*C12P 21/00* (2006.01)

(52) U.S. Cl. ............... 435/69.1; 435/70.1; 435/252.3; 435/320.1; 435/325; 435/71.1; 536/23.1; 536/23.5; 530/350

(58) Field of Classification Search ............... 530/300, 530/350; 536/23.1, 23.5; 435/69.1, 70.1, 435/252.3, 320.1, 325
See application file for complete search history.

(56) References Cited

U.S. PATENT DOCUMENTS

| | | | |
|---|---|---|---|
| 5,350,836 A | * | 9/1994 | Kopchick et al. ............ 530/399 |
| 5,948,676 A | * | 9/1999 | Chang et al. ............... 435/325 |
| 2003/0157095 A1 | | 8/2003 | Papadopoulos .......... 424/143.1 |

FOREIGN PATENT DOCUMENTS

| | | |
|---|---|---|
| WO | WO-9949316 A2 | 9/1999 |
| WO | WO-0001821 A2 | 1/2000 |
| WO | WO-0009549 A2 | 2/2000 |

OTHER PUBLICATIONS

Rao RM et al. Regulation of steroid hormone biosynthesis in R2C and MA-10 Leydig tumor cells: role of the cholesterol transfer proteins StAR and PBR. Endocr Res. 28(4):387-394, 2002.*
Papadopoulos, V et al. In vivo studies on the role of the peripheral benzodiazepine receptor (PBR) in steroidogenesis. Endocr Res. 24(3-4):479-487, 1998.*
Papadopoulos V et al. Peripheral benzodiazepine receptor in cholesterol transport and steroidogenesis. Steroids. 62(1):21-28, 1997.*
Papadopoulos V et al. Role of the peripheral-type benzodiazepine receptor and the polypeptide diazepam binding inhibitor in steroidogenesis, J Steroid Biochem Mol Biol. 53(1-6):103-110, 1995.*
Li, H et al. Peripheral-type benzodiazepine receptor function in cholesterol transport. Identification of a putative cholesterol recognition/interaction amino acid sequence and consensus pattern. Endocrinology. 139(12):4991-4997, 1998.*
Li, H e tal. Identification, localization, and function in steroidogenesis of PAP7: a peripheral-type benzodiazepine receptor- and PKA (RI alpha)-associated protein. Molec Endocrinol 15(12):2211-2228, 2001.*
Li et al. Accession No. AF022770, direct submission, Oct. 2, 1997.*
Zisterer et al. Identification of novel ligands for the peripheral-type benzodiazepine receptor. Biochem Soc Trans. 23(2):371S, 1995.*
Hauet et al. PBR, StAR, and PKA: partners in cholesterol transport in steroidogenic cells. Endocr Res. 28(4):395-401, 2002.*
Culty M et al. In vitro studies on the role of the peripheral-type benzodiazepine receptor in steroidogenesis. J Steroid Biochem Mol Biol. 69(1-6):123-130, 1999.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4):132-133, 1999.*
Smith et al. The challenges of genome sequence annotation or "The devil is in the details". Nature Biotech 15: 1222-1223, 1997.*
Brenner, S.E. Errors in genome function. Trends in Genetics 15(4):132-133, 1999.*

(Continued)

*Primary Examiner*—Elizabeth Kemmerer
*Assistant Examiner*—Bridget E. Bunner
(74) *Attorney, Agent, or Firm*—Schwegman, Lundberg, Woessner & Kluth, P.A.

(57) ABSTRACT

The present invention relates to nucleic acids encoding peripheral-type benzodiazepine receptor (PBR)-associated proteins (PAPs), and nucleic acids that hybridize or are variant of nucleic acids encoding the peripheral-type benzodiazepine receptor (PBR)-associated proteins (PAPs), which are capable of encoding proteins that regulate the function of PBRs affecting both steroid biosynthesis and mediating cholesterol delivery as well as other PBR-mediated functions.

13 Claims, 8 Drawing Sheets

OTHER PUBLICATIONS

Bork et al. Go hunting in sequence databases but watch out for the traps. Trends in Genetics. 12(10): 425-427, 1996.*

Wells. J.A. Additivity of mutational effects in proteins. Biochemistry 29 (37): 8509-8517, 1990.*

Ngo et al. Computational complexity, protein structure prediction, and the Levinthal paradox. The Protein Folding Problem and Tertiary Structure Prediction, pp. 492-495, 1994.*

Phillips, A. The challenge of gene therapy and DNA delivery. J Pharm Pharmcol 53: 1169-1174, 2001.*

Kapur et al. The presence of novel amino acids in the cytoplasmic domain of stem cell factor results in hematopoietic defects i Steel17H mice. Blood (94)6: 1915-1925, 1999.*

Sher et al. Mutations uncouple human fibroblast growth factor (FGF)-7 biological activity and receptor binding and support broad specificity in the secondary receptor binding site of FGFs. J Biol Chem 274(49): 35016-35022, 1999.*

Wuyts et al. NH2- and COOH-terminal truncations of murine granulocyte chemotactic protein-2 augment the in vitro and in vivo neutrophil chemotactic potency. J Immunol 163: 6155-6163, 1999.*

Li H et al. (2001) "Identification, localization, and function in steroidogenesis of PAP7: a peripheral-type benzodiazepine receptor- and PKA (RIalpha)-associated protein," *Mol Endocrinol* 15: 2211-28.

Don, J., "M. musculus mRNA megi", *Database EMBL [Online] AC X64455*, Jul. 26, 1993.

Galiegue, S. , et al., "Cloning and Characterization of PRAX-1—A New Protein that Specifically Interacts with the Peripheral Benzodiazepine Receptor", *The Journal of Biological Chemistry*, 274(5), (1999),2938-2952.

Garnier, M. , et al., "Diazepam Binding Inhibitor is a Paracrine/Autocrine Regulator of Leydig Cell Proliferation and Steroidogenesis: Action via Peripheral-Type Benzodiazepine Receptor and Independent Mechanisms", *Endocrinology*, 132(1), (1993),444-458.

Hardwick, M. , et al., "Abstract #1569 The Peripheral-type Benzodiazepine Receptor in Human Breast Cancer", *Proceedings of the American Association for Cancer Research*, 38 (1997),233.

Hardwick, M. , et al., "Peripheral-Type Benzodiazepine Receptor (PBR) in Human Breast Cancer: Correlation of Breast Cancer Cell Aggressive Phenotype with PBR Expression, Nuclear Localization, and PBR-mediated Cell Proliferation and Nuclear Transport of Cholesterol", *Cancer Research*, 59(4), (1999),831-842.

Kozikowski, A. P., et al., "Synthesis and Biology of a 7-Nitro-2,1,3-benzoxadiazol-4-yl Derivative of 2-Phenylindole-3-acetamide: A Fluorescent Probe for the Peripheral-Type Benzodiazepine Receptor", *Journal of Medicinal Chemistry*, 40(16), (1997),2435-2439.

Krueger, K. E., et al., "Peripheral-type Benzodiazepine Receptors Mediate Translocation of Cholesterol from Outer to Inner Mitochrondrial Membranes in Adrenocortical Cells", *The Journal of Biological Chemistry*, 265(25), (1990),15015-15022.

Li, H. , et al., "Mus musculus peripheral benzodiazepine receptor associated protein", *Database EMBL [Online] AC AF022770*, (Oct. 2, 1997).

Marra, M. , et al., "mo98e12.r1 Stratagene mouse testis (#937308) Mus musculus cDNA clone", *Database EMBL [Online] AC AA174581*, Mar. 3, 2000.

Miettinen, H. , et al., "Expression of Peripheral-Type Benzodiazepine Receptor and Diazepam Binding Inhibitor in Human Astrocytomas: Relationship to Cell Proliferation", *Cancer Research*, 55, (1995),26912695.

Moser, P. C., "Protentiation of 5-Methoxy-N,N-Dimethyltryptamine-Induced Head-Twitches by Diazepam: Evidence for Involvement of Adenosine Uptake Inhibition", *Drug Development Research*, 30(4), (1993),213-218.

Papadopoulos, V. , et al., "Targeted Disruption of the Peripheral-Type Benzodiazepine Receptor Gene Inhibits Steroidogenesis in the R2C Leydig Tumor Cell Line", *The Journal of Biological Chemistry*, 272(51), (1997),32129-32135.

Pawlikowski, M. , et al., "Inhibition of Cell Proliferation of Human Gliomas by Benzodiazepines *in vitro*", *Acta Neurol Scand.*, 77, (1988),231-233.

Sambrook, J. , et al., *Molecular Cloning—a Laborary Manual*, 2d Edition, Cold Spring Laboratory Press,(1989)9. 47-9.62.

Ahn, A. H., "The Structural and Functional Diversity of Dystrophin", *Nature Genetics*, 3, (Apr., 1993),283-291.

Boyle, T P., et al., "Structure of the murine gene encoding apolipoprotein A-1.", *Gene*, 117(2), (Aug. 15, 1992),243-7.

Cawthon, R. M., et al., "cDNA Sequence and Genomic Structure of EV12B, a Gene Lying within an Intron of the Neurofibromatosis Type 1 Gene", *Genomics*, 9, (1991),446-460.

Don, J , et al., "Identification and characterization of the regulated pattern of expression of a novel mouse gene, meg1, during the meiotic cell cycle", *Cell Growth Differ.*, 3(8), (Aug. 1992),495-505.

Don, J. et al., "M.musculus mRNA meg1", *Database EMBL AC X64455*, Jul. 26, 1993.

Ever, L , et al., "Two alternatively spliced Meig1 messenger RNA species are differentially expressed in the somatic and in the germ-cell compartments of the testis", *Cell Growth Differ.*, 10(1), (Jan. 1999),19-26.

Farges, R , et al., "Site-directed mutagenesis of the peripheral benzodiazepine receptor: identification of amino acids implicated in the binding site of Ro5-4864", *Mol. Pharmacol.*, 46(6), (Dec. 1994),1160-7.

Glenney, J R., et al., "The sequence of human caveolin reveals identity with VIP21, a component of transport vesicles.", *FEBS Letters*, 314(1), (Dec. 7, 1992),45-48.

Harris, P.C., et al., "Polycystic Kidney Disease 1: Identification and Analysis of the Primary Defect", *Journal of the American Society of Nephrology*, 6, (1995),1125-1133.

Hillier, L. D., et al., "zl87a08.r1 Stratagene colon (#937204) Homo sapiens cDNA clone", *AA127107— NCBI Database—Pubmed*, May 19, 1997.

Li, H. , et al., "Mus Musculus peripheral Benzodiazepine Receptor Associated protein(Pap20) MRNA, Partial cds.", *AF020338—NCBI Database—Pubmed*, Sep. 24, 1997.

Muzny, D. M., et al., "Homo-sapiens 12 PAC RPI-96H9 (Roswell Park Cancer Institute Human PAC Library) Complete Sequence", *AC006057—NCBI Database—Pubmed.* May 1, 1999.

Papadopoulos, V , "Structure and function of the peripheral-type benzodiazepine receptor in steroidogenic cells", *Proceedings of the Society for Experimental Biology & Medicine*, 217(2), (Feb. 2, 1998),130-142.

Pikuleva, I A., et al., "Active-site topology of bovine cholestrol side-chain cleavage cytochrome P450 (P450scc) and evidence for interaction of tyrosine 94 with the side chain of cholesterol", *Archives of Biochemistry and Biophysics*, 322(1), (Sep. 10, 1995), 189-97.

Su, P , et al., "A cDNA encoding a rat mitochondrial cytochrome P450 catalyzing both the 26-hydroxylation of vitamin D3: gonadotropic regulation of the cognate mRNA in ovaries", *DNA and Cell Biology* 9(9) , (Nov. 1990),657-67.

* cited by examiner

A

B

A

B

A

B

A

B

A

B

SEQUENCE LISTING

<160> NUMBER OF SEQ ID NOS: 11

<210> SEQ ID NO 1
<211> LENGTH: 505
<212> TYPE: DNA
<213> ORGANISM: Mus musculus

<400> SEQUENCE: 1

```
gattcgcggc cgcgtcgacc accgctgcgc cctcctgcga ggccggctga acgaggaaat      60
aattgctaat aaggcctctg tagccatggc tacttctgac gtgaaaccaa aatcaataag     120
tcgtgccaag aaatggtcag aggaaataga aaatctgtac agatttcaac aagcaggata    180
tcgggatgaa attgaatata aacaagtgaa acaagttgcc atggtcgacc gatggccaga    240
gacagggtac gtgaagaaac ttcagcggag ggacaatact ttcttctact acaacaaaga    300
gagggagtgc gaggacaagg aggtccacaa agtgaaggtt tacgtctact gacctttttcc   360 tttcttcggc ttggcaatgc tcctttaaga attggttgtt tacattcttc catcgtgtaa    420
atgtcatttt acaaaacaat tcacaattct gtctttaatt catggtgtct tacacaacat    480
aaacacccac cttgaaaccc aaaaa                                          505
```

<210> SEQ ID NO 2
<211> LENGTH: 1459
<212> TYPE: DNA
<213> ORGANISM: Mus musculus

<400> SEQUENCE: 2

```
gaattcgcgg ccgcgtcgac ctaaagttga gttgttcact gtagtgaccc gtgtgaaggt     60 agttttatttt taaatcaac tttcattgtg caaactagta aaagatggca aagcctttca    120
tccaacttat gaagaaaaac tgaagttcgt ggcactgcat aagcaagttc ttttgggccc    180
atataaccca gacacgtccc ctgaggttgg attctttgat gtgttgggga atgataggag    240
gagagaatgg gcagctctgg gaaacatgtc caaggaggat gccatggtag agttttgtgaa    300 gcttctaaat aagtgttgtc ctctcctctc ggcatatgtt gcgtcccaca gaatagagaa    360
ggaagaagaa gagaaaagaa gaaaggcgga ggaggagcga aggcagcgtg aagaggaaga    420
acgagagcgg ctgcaaaagg aagaagagaa gcggaagcga gaggaggaag accggctgag   480
acgggaggag gaagagaggc ggcggataga ggaagagagg cttcggctgg aacagcaaaa    540
gcagcagata atggcagctt taaactcgca gactgccgtg caattccagc agtatgcagc    600
ccagcagtat ccagggaact acgaacaaca gcagattctc atccgccagc tgcaggagca    660
```

```
gcactatcag cagtataaac accaggcaga gcaaacccaa cctgcacaac aacaggcagc    720
attacagaaa cagcaagaag tagtgatggc tggggcatca ttgcctgcat catcaaaggt    780
gaacacagct ggagcaagtg atacactgtc agttaatgga caggccaaaa cccacactga    840
aaattccgaa aaagtccttg agccagaagc tgcagaagaa gccttggaaa atggaccaaa    900
agactctctt ccagtgattg cagctccatc catgtggaca agaccacaaa tcaaagactt    960
taaagagaag attcggcagg atgcagattc tgtgattaca gtacgtcgag agaagtcgt    1020 caccgtccga gtcccgactc atgaggaagg atcataccta ttttgggaat tgccacaga    1080 cagttatgac attgggtttg gggtttattt tgaatggaca gactctccaa atgctgctgt    1140
cagtgtgcat gtcagtgagt ccagtgacga ggaggaggag gaggaagaaa atgtcacttg    1200
tgaagaaaaa gcaaaaaaga acgccaacaa gcctctgctg gatgagattg tacctgtgta    1260
ccggcgggac tgtcacgagg aagtatatgc aggcagccac cagtatccag ggaggggagt    1320
ctatctcctc aagtttgata attcctactc tctgtggagg tccaagtccg tctactacag    1380
agtctattat actagataga gctgctgttc caaggtccgg agtccagggt tgagcacaac    1440
atgacgttta atttccttt                                                1459

<210> SEQ ID NO 3
<211> LENGTH: 568
<212> TYPE: DNA
<213> ORGANISM: Mus musculus

<400> SEQUENCE: 3
gaattcgcgg ccgcgtcgac gctggacaca agcgtggagc gaagagccct ggagagatt     60 cagaatgtag gtgaaggctc ttcaacatca cagggcacct gcagtcttc agagtcctca    120 cagtcaaacc tgggggagca gacgcagagc ggaccccagg gaggaaggtg tcagcgtcgg    180
gagaggcata accgaatgga acgagatagg aggcgcagaa tccgcatttg ctgtgatgag    240
ctgaatcttt tagttccatt ctgcaatgcg agacagata aagcaacaac ccttcagtgg    300
accacagcat tcctgaagta cattcaggaa agacatgggg actctcttaa aaaggaattt    360
gagagcgtgt tttgcggtaa aactggcaga aggctaaagc tgactagacc cgaatccctg    420
gtgacctgcc ctgcacaggg cagcctgcag agcagccctg ccatggagat caagtgactg    480
gactgaccca ggacctggga gagaaccgcc gttcctgcgg catcatgcac atgcctgcca    540
tccccggaat tcagctctga atcctctc                                      568

<210> SEQ ID NO 4
<211> LENGTH: 490
<212> TYPE: DNA
<213> ORGANISM: Mus musculus

<400> SEQUENCE: 4
gaattcgcgg ccgcgtcgac ctcggggta accttggga tcattatgat gtcacctctt      60
caatctcttg agaccagtga tttatgaact tgacatttgg tgcctggtgt gggctttgga    120
aagcagaggc cacctttgtc tgtagaggat actgagcggc tggatggcag gaatccaaag    180
agaagccagc ctctcgtagt cgccctggga cagtggaaga gagggaggac cggcaaaggg    240
gaatctgtct ttctcctagg cccgagcatg tcccctgtgg acatgctct gtgacagctg    300 agcctgccca gcctgccttt ctgaagttgg gtgtctcctg cccacaacca agccagcaat    360
cggtctgttt tccgacaacc tcagagccag acctcacaag cctatttgg tggttcccaa    420 aatttctctc agatctccat gtctatccct ccactccctc caaaagagaa agaaaagaat    480
```
tgagaaagaa                                                              490

<210> SEQ ID NO 5
<211> LENGTH: 588
<212> TYPE: DNA
<213> ORGANISM: Mus musculus

<400> SEQUENCE: 5
gaattcgcgg ccgcgtcgac ctcagaagag gaaagaggt gcagaagtgc tggcggcaca      60
aattgtacag aaaccagac tagagagaaa aaacaagaa gcgtctgtat ctaaagatgc      120
tccagtgcct acaaatacta aagggcaaa gaaacaagag aagtctccag gtagaattgc      180
ctcacagtct aagccaccca tgaaaaagtc tccacaaaaa cggaaggtaa atgtagcaag      240
aggccgtcgg aataccagaa agcagctcca acctgccgaa aaagaaattg ctttacatct      300
tcaatcagaa atttcatcag atggccaaaa agatggactt aacctaagta catctcaaca      360
agaaagtatt tcaatgattc ctaaaggtcc tcctgaaaac tcagttatca gctgtgactc      420
ccaggcccta aatatgttag ctgatctggc attaagttct gctgctgctt ctataccatc      480
ttgtaagccc aggaaccttc cctgcgtctc tgatttgcca cgaaacaatg tcttactcac      540
taaagaaaat ccattgcttg gtgcctctga ccatgaatat cataaggg                  588

<210> SEQ ID NO 6
<211> LENGTH: 88
<212> TYPE: PRT
<213> ORGANISM: Mus musculus

<400> SEQUENCE: 6

Met Ala Thr Ser Asp Val Lys Pro Lys Ser Ile Ser Arg Ala Lys Lys
 1               5                  10                  15

Trp Ser Glu Glu Ile Glu Asn Leu Tyr Arg Phe Gln Gln Ala Gly Tyr
            20                  25                  30

Arg Asp Glu Ile Glu Tyr Lys Gln Val Lys Gln Val Ala Met Val Asp
        35                  40                  45

Arg Trp Pro Glu Thr Gly Tyr Val Lys Lys Leu Gln Arg Arg Asp Asn
    50                  55                  60

Thr Phe Phe Tyr Tyr Asn Lys Glu Arg Glu Cys Glu Asp Lys Glu Val
65                  70                  75                  80

His Lys Val Lys Val Tyr Val Tyr
                85

<210> SEQ ID NO 7
<211> LENGTH: 463
<212> TYPE: PRT
<213> ORGANISM: Mus musculus

<400> SEQUENCE: 7

Arg Pro Arg Arg Pro Lys Val Glu Leu Phe Thr Val Val Thr Arg Val
 1               5                  10                  15

Lys Val Val Leu Phe Leu Asn Gln Leu Ser Leu Cys Lys Leu Val Lys
            20                  25                  30

Asp Gly Lys Ala Phe His Pro Thr Tyr Glu Glu Lys Leu Lys Phe Val
        35                  40                  45

Ala Leu His Lys Gln Val Leu Leu Gly Pro Tyr Asn Pro Asp Thr Ser
    50                  55                  60

Pro Glu Val Gly Phe Phe Asp Val Leu Gly Asn Asp Arg Arg Arg Glu
65                  70                  75                  80

```
Trp Ala Ala Leu Gly Asn Met Ser Lys Glu Asp Ala Met Val Glu Phe
             85                  90                  95

Val Lys Leu Leu Asn Lys Cys Cys Pro Leu Ser Ala Tyr Val Ala
            100                 105                 110

Ser His Arg Ile Glu Lys Glu Glu Glu Lys Arg Lys Ala Glu
            115                 120                 125

Glu Glu Arg Arg Gln Arg Glu Glu Glu Arg Glu Arg Leu Gln Lys
    130                 135                 140

Glu Glu Glu Lys Arg Lys Arg Glu Glu Asp Arg Leu Arg Arg Glu
145                 150                 155                 160

Glu Glu Glu Arg Arg Arg Ile Glu Glu Arg Leu Arg Leu Glu Gln
                165                 170                 175

Gln Lys Gln Gln Ile Met Ala Ala Leu Asn Ser Gln Thr Ala Val Gln
                180                 185                 190

Phe Gln Gln Tyr Ala Ala Gln Gln Tyr Pro Gly Asn Tyr Glu Gln Gln
        195                 200                 205

Gln Ile Leu Ile Arg Gln Leu Gln Glu Gln His Tyr Gln Gln Tyr Lys
        210                 215                 220

His Gln Ala Glu Gln Thr Gln Pro Ala Gln Gln Ala Ala Leu Gln
225                 230                 235                 240

Lys Gln Gln Glu Val Val Met Ala Gly Ala Ser Leu Pro Ala Ser Ser
                245                 250                 255

Lys Val Asn Thr Ala Gly Ala Ser Asp Thr Leu Ser Val Asn Gly Gln
                260                 265                 270

Ala Lys Thr His Thr Glu Asn Ser Glu Lys Val Leu Glu Pro Glu Ala
            275                 280                 285

Ala Glu Glu Ala Leu Glu Asn Gly Pro Lys Asp Ser Leu Pro Val Ile
290                 295                 300

Ala Ala Pro Ser Met Trp Thr Arg Pro Gln Ile Lys Asp Phe Lys Glu
305                 310                 315                 320

Lys Ile Arg Gln Asp Ala Asp Ser Val Ile Thr Val Arg Arg Gly Glu
                325                 330                 335

Val Val Thr Val Arg Val Pro Thr His Glu Glu Gly Ser Tyr Leu Phe
                340                 345                 350

Trp Glu Phe Ala Thr Asp Ser Tyr Asp Ile Gly Phe Gly Val Tyr Phe
        355                 360                 365

Glu Trp Thr Asp Ser Pro Asn Ala Ala Val Ser Val His Val Ser Glu
    370                 375                 380

Ser Ser Asp Glu Glu Glu Glu Glu Asn Val Thr Cys Glu Glu
385                 390                 395                 400

Lys Ala Lys Lys Asn Ala Asn Lys Pro Leu Leu Asp Glu Ile Val Pro
                405                 410                 415

Val Tyr Arg Arg Asp Cys His Glu Glu Val Tyr Ala Gly Ser His Gln
            420                 425                 430

Tyr Pro Gly Arg Gly Val Tyr Leu Leu Lys Phe Asp Asn Ser Tyr Ser
        435                 440                 445

Leu Trp Arg Ser Lys Ser Val Tyr Tyr Arg Val Tyr Tyr Thr Arg
        450                 455                 460

<210> SEQ ID NO 8
<211> LENGTH: 158
<212> TYPE: PRT
<213> ORGANISM: Mus musculus
```

-continued

<400> SEQUENCE: 8

```
Glu Phe Ala Ala Ala Ser Thr Leu Asp Thr Ser Val Glu Arg Arg Ala
  1               5                  10                  15

Leu Gly Glu Ile Gln Asn Val Gly Gly Ser Ser Thr Ser Gln Gly
             20                  25                  30

Thr Trp Gln Ser Ser Glu Ser Ser Gln Ser Asn Leu Gly Glu Gln Thr
         35                  40                  45

Gln Ser Gly Pro Gln Gly Gly Arg Cys Gln Arg Glu Arg His Asn
     50                  55                  60

Arg Met Glu Arg Asp Arg Arg Arg Ile Arg Ile Cys Cys Asp Glu
 65                  70                  75                  80

Leu Asn Leu Leu Val Pro Phe Cys Asn Ala Glu Thr Asp Lys Ala Thr
                 85                  90                  95

Thr Leu Gln Trp Thr Thr Ala Phe Leu Lys Tyr Ile Gln Glu Arg His
             100                 105                 110

Gly Asp Ser Leu Lys Lys Glu Phe Glu Ser Val Phe Cys Gly Lys Thr
             115                 120                 125

Gly Arg Arg Leu Lys Leu Thr Arg Pro Glu Ser Leu Val Thr Cys Pro
130                 135                 140

Ala Gln Gly Ser Leu Gln Ser Ser Pro Ala Met Glu Ile Lys
145                 150                 155
```

<210> SEQ ID NO 9
<211> LENGTH: 112
<212> TYPE: PRT
<213> ORGANISM: Mus musculus

<400> SEQUENCE: 9

```
Ala Ala Gly Trp Gln Glu Ser Lys Glu Lys Pro Ala Ser Arg Ser Arg
  1               5                  10                  15

Pro Gly Thr Val Glu Glu Arg Glu Asp Arg Gln Arg Gly Ile Cys Leu
             20                  25                  30

Ser Pro Arg Pro Glu His Val Pro Cys Gly Thr Cys Ser Val Thr Ala
         35                  40                  45

Glu Pro Ala Gln Pro Ala Phe Leu Lys Leu Gly Val Ser Cys Pro Gln
     50                  55                  60

Pro Ser Gln Gln Ser Val Cys Phe Pro Thr Thr Ser Glu Pro Asp Leu
 65                  70                  75                  80

Thr Ser Leu Phe Trp Trp Phe Pro Lys Phe Leu Ser Asp Leu His Val
                 85                  90                  95

Tyr Pro Ser Thr Pro Ser Lys Arg Glu Arg Lys Glu Leu Arg Lys Lys
             100                 105                 110
```

<210> SEQ ID NO 10
<211> LENGTH: 196
<212> TYPE: PRT
<213> ORGANISM: Mus musculus

<400> SEQUENCE: 10

```
Asn Ser Arg Pro Arg Arg Pro Gln Lys Arg Lys Arg Gly Ala Glu Val
  1               5                  10                  15

Leu Ala Ala Gln Ile Val Gln Lys Thr Arg Leu Glu Arg Lys Lys Gln
             20                  25                  30

Glu Ala Ser Val Ser Lys Asp Ala Pro Val Pro Thr Asn Thr Lys Arg
         35                  40                  45

Ala Lys Lys Gln Glu Lys Ser Pro Gly Arg Ile Ala Ser Gln Ser Lys
```

-continued

```
                50                   55                   60
Pro Pro Met Lys Lys Ser Pro Gln Lys Arg Lys Val Asn Val Ala Arg
 65                  70                  75                  80

Gly Arg Arg Asn Thr Arg Lys Gln Leu Gln Pro Ala Glu Lys Glu Ile
                 85                  90                  95

Ala Leu His Leu Gln Ser Glu Ile Ser Ser Asp Gly Gln Lys Asp Gly
                100                 105                 110

Leu Asn Leu Ser Thr Ser Gln Gln Glu Ser Ile Ser Met Ile Pro Lys
                115                 120                 125

Gly Pro Pro Glu Asn Ser Val Ile Ser Cys Asp Ser Gln Ala Leu Asn
                130                 135                 140

Met Leu Ala Asp Leu Ala Leu Ser Ser Ala Ala Ala Ser Ile Pro Ser
145                 150                 155                 160

Cys Lys Pro Arg Asn Leu Pro Cys Val Ser Asp Leu Pro Arg Asn Asn
                165                 170                 175

Val Leu Leu Thr Lys Glu Asn Pro Leu Leu Gly Ala Ser Asp His Glu
                180                 185                 190

Tyr His Lys Gly
        195

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Ser Ser Asp Glu Glu Glu Glu Glu Glu Asn Val Thr Cys Glu Glu
  1               5                  10                  15

Lys Ala Lys Lys Asn Ala Asn Lys Pro
                 20                  25
```

DNA ENCODING PERIPHERAL-TYPE BENZODIAZIPINE RECEPTOR ASSOCIATED PROTEIN 7 AND APPLICATIONS OR METHODS OF USE

CLAIM OF PRIORITY

This application is a continuation application under 35 U.S.C. § 371 of International Application No. PCT/US99/18507 filed Aug. 11, 1999 and published in English as WO 00/09549 on Feb. 24, 2000, which in turn claims priority to U.S. provisional patent application No. 60/096,048, filed Aug. 11, 1998, the disclosures of which applications and publication are incorporated by reference herein.

This claims benefit of Ser. No. 60/096,048 filed Aug. 11, 1998.

STATEMENT OF GOVERNMENT FUNDING

The work described herein was funded, in whole or in part, by The National Institutes of Health, Grant No. HD37031. The United States Government has certain rights in the invention.

FIELD OF THE INVENTION

The present invention relates to nucleic acid molecules encoding peripheral-type benzodiazepine receptor (PBR) associated proteins (PAPs), including mutants, variants, fragments and derivatives thereof, and to vectors and host cells comprising such nucleic acid molecules; methods of using PAPs; method for screening for inhibitors and activators of PAPs or PBR; and kits comprising the compositions or polypeptides of the invention.

BACKGROUND OF THE INVENTION

The peripheral-type benzodiazepine receptor (PBR) was originally discovered because it binds the benzodiazepine diazepam with relatively high affinity (Papadopoulos, V. 1993, *Endocr. Rev.* 14:222–240). Benzodiazepines are among the most highly prescribed drugs due to their pharmacological actions in relieving anxiety mediated through modulating the activity of γ-aminobutyric acid receptors in the central nervous system (Costa, E. and Guidotti, A. 1979, *Annu. Rev. Pharmacol. Toxicol.* 19:531–545). PBR is another class of binding sites for benzodiazepines distinct from the aforementioned neurotransmitter receptors. Further studies demonstrated that in addition to benzodiazepines, PBR binds other classes of organic compounds with high affinity (Papadopoulos, 1993, supra). PBR, although present in all tissues examined, was found to be particularly high in steroid producing tissues, where it was primarily localized in the outer mitochondrial membrane (OMM) (Anholt, R. R. H. et al. 1986, *J. Biol. Chem.* 261:576–583). An 18 kDa isoquinoline-binding protein was identified as PBR, cloned and expressed (Papadopoulos, V. 1998, *Proc Soc. Exp. Biol. Med.* 217:130–142). It was then demonstrated that PBR is a functional component of the steroidogenic machinery (Papadopoulos, 1998, supra; Papadopoulos V. et al. 1990, *J. Biol. Chem.* 265:3772–3779) mediating cholesterol delivery from the outer to the inner mitochondrial membrane (Krueger, K. E. and Papadopoulos, V. 1990, *J. Biol. Chem.* 265:15015–15022). Further studies demonstrated that pharmacologically induced reduction of adrenal PBR levels in vivo resulted in decreased circulating glucocorticoid levels (Papadopoulos, V. 1998, supra) In addition, targeted disruption of the PBR gene in Leydig cells resulted in the arrest of cholesterol transport into mitochondria and steroid formation; transfection of the mutant cells with a PBR cDNA rescued steroidogenesis (Papadopoulos, V. et al. 1997, *J. Biol. Chem.* 272:32129–32135).

PBR is extremely abundant in steroidogenic cells and found primarily on outer mitochondrial membranes (Anholt, R. et al. 1986, *J. Biol. Chem.* 261:576–583). PBR is thought to be associated with a multimeric complex composed of the 18-kDa isoquinoline-binding protein and the 34-kDa pore-forming voltage-dependent anion channel protein, preferentially located on the outer/inner mitochondrial membrane contact sites (McEnery, M. W. et al. *Proc. Natl. Acad. Sci. U.S.A.* 89:3170–3174; Garnier, M. et al. 1994, *Mol. Pharmacol.* 45:201–211; Papadopoulos, V. et al. 1994, *Mol. Cel. Endocr.* 104:R5–R9). Drug ligands of PBR, upon binding to the receptor, simulate steroid synthesis in steroidogenic cells in vitro (Papadopoulos, V. et al. 1990, *J. Biol. Chem.* 265:3772–3779; Ritta, M. N. et al. 1989, *Neuroendocrinology* 49: 262–266; Barnea, E. R. et al. 1989, *Mol. Cell. Endocr.* 64:155–159; Amsterdam, A. and Suh, B. S. 1991, *Endocrinology* 128:503–510; Yanagibashi, K. et al. 1989, *J. Biochem.* (*Tokyo*) 106: 1026–1029). Likewise, in vivo studies showed that high affinity PBR ligands increase steroid plasma levels in hypophysectomized rats (Amri, H. et al. 1996, *Endocrinology* 137:5707–5718). Further in vitro studies on isolated mitochondria provided evidence that PBR ligands, drug ligands, or the endogenous PBR ligand, the polypeptide diazepam-binding inhibitor (BDI) (Papadopoulos, V. et al. 1997, *Steroids* 62:21–28), stimulate pregnenolone formation by increasing the rate of cholesterol transfer from the outer to the inner mitochondrial membrane (Krueger, K. E. and Papadopoulos, V. 1990, *J. Biol. Chem.* 265:15015–15022; Yanagibashi, K. et al. 1988, *Endocrinology* 123: 2075–2082; Besman, M. J. et al. 1989, *Proc. Natl. Acad. Sci. U.S.A.* 86: 4897–4901; Papadopoulos, V. et al. 1991, *Endocrinology* 129: 1481–1488).

Based on the amino acid sequence of the 18-kDa PBR, a three dimensional model was developed (Papadopoulos, V. 1996, In: *The Leydig Cell*. Payne, A. H. et al. (eds) Cache River Press, IL, pp 596–628). This model was shown to accomodate a cholesterol molecule and function as a channel, supporting the role of PBR in cholesterol transport. Recently we demonstrated the role of PBR in steroidogenesis by generating PBR negative cells by homologous recombination (Papadopoulos, V. et al. 1997, *J. Biol. Chem.* 272:32129–32135) that failed to produce steroids. However, addition of the hydrosoluble analogue of cholesterol, 22R-hydroxycholesterol, recovered steroid production by these cells, indicating that the cholesterol transport mechanism was impaired. Further cholesterol transport experiments in bacteria expressing the 18-kDa PBR protein provided definitive evidence for a function as a cholesterol channel/transporter (Li and Papadopoulos, 1998, *Endocrinology* 139, 4991–4997).

Studies in a number of tumors such as rat brain containing glioma tumors (Richfield, E. K. et al. 1988, *Neurology* 38:1255–1262), colonic adenocarcinoma and ovarian carcinoma (Katz, Y. et al. 1988, *Eur. J. Pharmacol.* 148: 483–484 and Katz, Y. et al. 1990, *Clinical Sci.* 78:155–158) have shown an abundance of peripheral-type benzodiazepine receptors (PBR) compared to normal tissue. All documents cited herein infra and supra are hereby incorporated in their entirety by reference thereto. Moreover, a 12-fold increase in PBR density relative to normal parenchyma, was found in human brain glioma or astrocytoma (Cornu, P. et al. 1992, *Acta Neurochir.* 119:146–152). The authors suggested that PBR densities may reflect the proliferative activity of the receptor in these tissues. Recently, the involvement of PBR in cell proliferation was further shown (Neary, J. T. et al. 1995, *Brain Research* 675:27–30; Miettinen, H. et al. 1995, *Cancer Research* 55:2691–2695), and its expression in human astrocytic tumors was found to be associated with tumor malignancy and proliferative index (Miettinen, H. et al. supra; Alho, H. 1994, *Cell Growth Different.* 5:1005–1014). Characterization of PBR in human breast cancer biopsies, led to the discovery that the invasive and metastatic ability of human breast tumor cells is proportional to the level of PBR expressed, and correlates with the subcellular localization of PBR in these cells in that PBR is found primarily in the nucleus in aggressive tumor cells whereas PBR is found primarily in the cytoplasm of invasive but non-aggressive cells. These changes in PBR expression can be used as a tool for detection, diagnosis, prevention and treatment in breast cancer patients, in particular, and in aggressive solid tumors in general.

Since both PBR and its endogenous ligand, the polypeptide diazepam binding inhibitor, are constitutively expressed in steroidogenic cells, the regulation of PBR function by hormones may be due to its association with other proteins. This interaction may result in the initiation of steroid biosynthesis. Therefore, there is a need to identify proteins which associate with PBR and may modulate PBR function.

SUMMARY OF THE INVENTION

The present invention meets the need described above. We have identified PBR associated proteins (PAPs) that interact with PBR using the two-hybrid system. We used PBR as a bait to screen a mouse testis cDNA library. Five clones were isolated by their ability to interact with PBR: PAP3, PAP7, PAP8, PAP15, and PAP20. Among the nucleotide sequences identified, PAP3 was identical to the previously isolated meg1 protein (Don, J. and Wolgemuth, D. J., 1992, *Cell Growth Differ.* 3, 495; Ever, L. et al., 1999, *Cell Growth Differ.* 10, 19–26). PAP7, PAP8, PAP15, and PAP20 are novel sequences according to a search in the Genebank database which did not find a match for these sequences. PAP7 and PAP17 are different clones of the same novel protein product. All PAPs have fatty acylation (myristoylation) sites and PKC phosphorylation sites. In addition, PAP20 has a PKA phosphorylation site. The distribution and function of the PAPs, as well as their functional relationship to PBR is under investigation.

So far, the distribution of PAP7 in major mouse tissues such as brain, testis, ovary, adrenal, kidney and muscle showed a profile similar to the broader expression pattern of PBR, with an expression level paralleling the steroidogenic ability of the tissue. These data imply a role for these PAPs in the regulation of PBR function, serving as endogenous ligands or allosteric modulators of the receptor.

Therefore, it is an object of the present invention to provide novel DNA fragments encoding PBR associated proteins, PAP3 (SEQ ID NO:1), PAP-7 (SEQ ID NO:2) PAP8 (SEQ ID NO:3), PAP15 (SEQ ID NO:4), and PAP20 (SEQ ID NO:5). The DNA fragment is useful as a diagnostic agent for detection of nucleic acid sequences encoding PBR-associated proteins, as an agent for preparation of the protein encoded by the DNA, for the preparation of sequences encoding PAPs, whether cDNA or genomic, and as therapeutic agents.

It is another object of the invention to provide an amino acid sequence for PAPs encoded by the DNA sequences described above.

It is another object of the invention to provide a recombinant vector comprising a vector and the above described DNA fragments.

It is a further object of the present invention to provide a host cell transformed with the above-described recombinant DNA construct.

It is another object of the present invention to provide a method for producing PAPs which comprises culturing a host cell under conditions such that the above-described DNA fragment is expressed and a PAP is thereby produced, and isolating the PAP for use as a reagent, for example for screening drugs and inhibitors of PBR or the PAP itself, for diagnosis, and for therapy.

It is a further object of the present invention to provide an antibody to the above-described recombinant PAPs.

It is yet another object of the present invention to provide a method for detecting any of PAP3, PAP7, PAP8, PAP15, or PAP20 in a sample comprising:

(i) contacting a sample with antibodies which recognize any one of the PAPs mentioned above; and (ii) detecting the presence or absence of a complex formed between the PAP and antibodies specific therefor.

It is a further object of the present invention to provide a diagnostic kit comprising an antibody against PAP and ancillary reagents suitable for use in detecting the presence of PAP in cells, tissue or serum from yeast, mammals, animals, birds, fish, and plants.

It is yet another object of the present invention to provide a method for the detection of PAP from a sample using the polymerase chain reaction.

It is a further object of the present invention to provide a diagnostic kit comprising primers or oligonucleotides specific for PAP RNA or cDNA suitable for hybridization to PAP RNA or cDNA and/or amplification of PAP sequences and ancillary reagents suitable for use in detecting PAP RNA/cDNA in mammalian tissue.

It is yet another object of the present invention to provide a method for the detection of a PAP in a sample which comprises assaying for the presence or absence of PAP RNA or cDNA in a sample by hybridization assays.

It is an object of the present invention to provide a method for the measurement of PBR in a sample. The method comprises measuring the presence of a PAP complexed with PBR.

It is yet another object of the present invention to provide a method for modulating the function or altering the targeting of PBR by increasing or decreasing interaction of PBR with a PAP. PBR functions which can be modulated include cholesterol transport into the cell, steroid production, cell proliferation, and embryogenesis.

It is still another object of the present invention to provide a method for increasing or decreasing PBR function or expression in a cell by providing into the cell a PAP such that PBR function is increased or decreased.

It is yet another object of the present invention to provide a method for increasing or reducing steroidogenesis by altering the level of PAP in said cell.

It is still another object of the invention to provide a therapeutic method for the treatment or amelioration of diseases resulting from increased cell proliferation resulting from aberrant PBR function or expression or localization, said method comprising providing to an individual in need of such treatment an effective amount of a PAP, in a pharmaceutically acceptable diluent, of a PAP such that the aberrant PBR expression, function or localization, is corrected.

It is another object of the present invention to provide a therapeutic method for the treatment or amelioration of diseases resulting from decreased cell proliferation, said method comprising providing to an individual in need of such treatment an effective amount of PAP or an antibody against PAP or an agent which inhibits PAP expression or function in a pharmaceutically acceptable excipient.

It is another object of the present invention to provide a therapeutic method for the treatment or amelioration of diseases resulting from decreased or increased steroidogenesis, said method comprising providing to an individual in need of such treatment an effective amount of a PAP or an antibody against PAP or an agent which inhibits or activates PAP expression or function in a pharmaceutically acceptable diluent.

It is yet a further object of the present invention to provide a cDNA sequence encoding PAPs and vectors incorporating all or a fragment of said sequence, and cells, prokaryotic and eukaryotic, transformed or transfected with said vectors, for use in screening agents and drugs which inhibit expression or function of PAPs or PBR in such cells.

BRIEF DESCRIPTION OF THE DRAWINGS

These and other features, aspects, and advantages of the present invention will become better understood with reference to the following description and appended claims, and accompanying drawings where:

DETAILED DESCRIPTION

Figure 1:
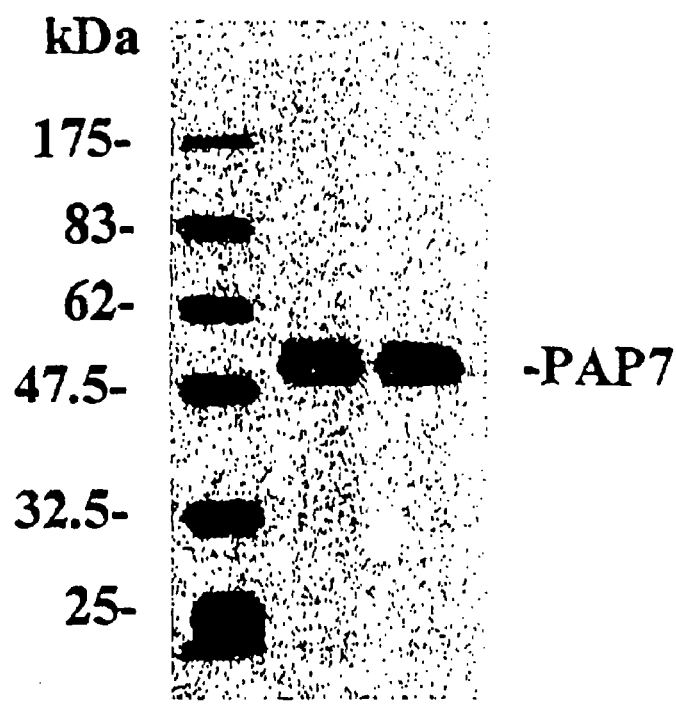
FIG. 1. PAP7 protein expressed in MA10 mouse Leydig tumor cells. (A) Western blot. (B), Immunocytochemistry.
Figure 1:
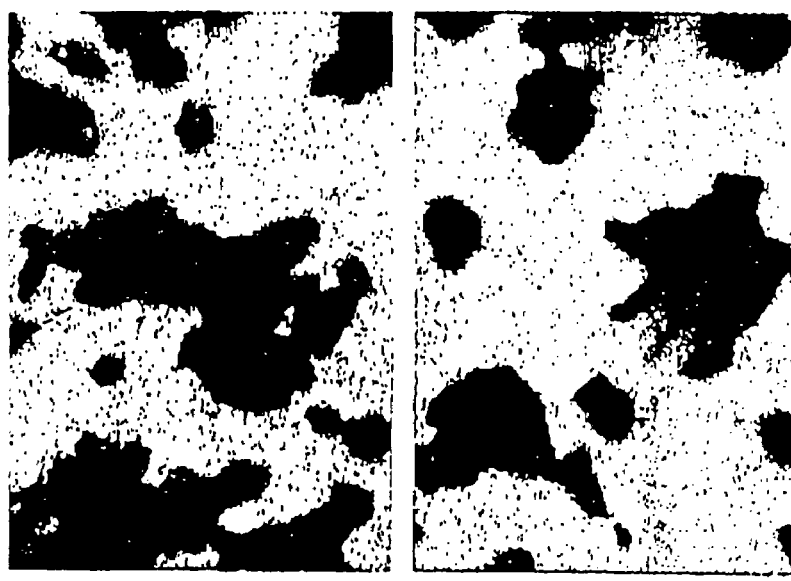

The five PAPs described in this application were discovered using a two-hybrid assay. The two-hybrid assay is a yeast-based genetic assay used to detect protein—protein interactions in vivo. A positive result obtained with the two-hybrid assay allows rapid identification of genes encoding proteins that interact with a target protein. In addition the two-hybrid assay is a sensitive method for detecting weak and transient interactions, which are probably the norm in large native complexes. Most notably, because the two-hybrid assay is performed in vivo, the proteins involved are more likely to be in their native conformations.

The two-hybrid assay is based on the fact that many eukaryotic transcriptional activators consist of two physically separable modular domains: one acts as the DNA-binding domain, while the other functions as the transcriptional activation domain. The DNA-binding domain localizes the transcription factor to specific DNA sequences present in the upstream region of genes that are regulated by this factor, while the activation domain contacts other components of the transcription machinery required to initiate transcription. Both domains are required for normal activation functioning, and normally the two domains are part of the same protein.

In our PAPs screening experiment, the MATCHMAKER Two-Hybrid System from CLONTECH was used. In the MATCHMAKER System, sequences encoding the two functional domains of the GAL4 transcriptional activator have been cloned into two different shuttle/expression vectors (pGBT9 and pGAD10). The pGBT9 hybrid cloning vector is used to generate a fusion of the GAL4 DNA-binding domain with PBR protein. The pGAD10 hybrid cloning vector is used to generate a fusion of the GAL4 activation domain with a collection of random proteins in a fusion mouse testis library (CLONTECH). Both hybrid proteins are targeted to the yeast nucleus by nuclear localization sequences that either are an intrinsic part of the GAL4 DNA-binding domain or have been added to the activation domain from a heterologous source. If PBR protein and an unknown protein or proteins interact with each other, the DNA-binding domain of GAL4 will be tethered to its transcriptional activation domain, and the proper function of the transcription of an appropriate reporter gene (lacz or HIS3) containing upstream GAL4 binding sites is used to indicate interaction between the two proteins. This allows a positive selection for clones that are transformed by two interacting hybrid constructs and makes library screening more convenient and practical. After a positive clone has been identified, the gene corresponding to the interacting protein was sequenced using the sequencing primers provided in the kit.

In one embodiment, the present invention relates to a DNA or cDNA sequence encoding PBR associated proteins (PAPs). Five clones were isolated, PAP3, comprising 568 bp and identified in SEQ ID NO:1 (Don, J. and Wolgemuth, D.

J., 1992, *Cell Growth Differ.* 3, 495; Ever, L. et al., 1999, *Cell Growth Differ.* 10, 19–26) which encodes a peptide of 83 amino acids identified in SEQ ID NO:6; PAP7, comprising 577 bp extending from 696 to 1164 of the sequence identified in SEQ ID NO:2, which encodes a polypeptide of 363 amino acids, identified in SEQ ID NO:7; PAP8, comprising 568 bp identified in SEQ ID NO:3, which encode a polypeptide of 190 amino acids, identified in SEQ ID NO:8; PAP15 comprising 490 bp identified in SEQ ID NO:4, which encode a polypeptide of 164 amino acids, identified in SEQ ID NO:9; and PAP20 comprising 588 bp identified in SEQ ID NO:5, which encode a polypeptide of 196 amino acids, identified in SEQ ID NO:10.

PAP3 has been identified as the previously isolated meg 1 protein.

PAP7 and PAP17 are different clones of the same novel protein product. Additional PAP7 sequence has been obtained using the 5', 3'RACE system (CLONTECH) and the near full-length gene is identified in SEQ ID NO:2 including the stop codon and some untranslated sequence at the 3' end. The polypeptide encoded by the DNA sequence would have a calculated molecular weight of about 50 kD. Using an PAP7 antibody produced from the initial isolated DNA fragment of 577 bp, a protein of about 52 kD is immunoprecipitated as shown in the Examples below. Analysis of the protein sequence indicates several concensus sequences and important sites such as: two potential myristoylation sites at positions 262–267 and 271–276 of SEQ ID NO:7 and five PKC phosphorylation sites at 395–396, 113–115, 255–257, 280–282, 331–333, and 339–341 of SEQ ID NO:7, an Acyl-Co-A site at position 24–108 of SEQ ID NO:7, a nuclear localization domain at position 150–167 of SEQ ID NO:7, a troponin site at position 98–247 of SEQ ID NO:2 and an HSP90 domain at position 126–155 of SEQ ID NO:7. The distribution and expression of PAP7 were examined in major mouse tissues such as brain, testis, ovary, adrenal, and kidney, as well as in tissue culture cell lines such as mouse C6 glioma cells, MA-10 Leydig cells, and Y1 adrenal cortical cells. The PAP7 expression pattern is similar to the broader expression profile of PBR in both tissues and cell lines involved in steroid biosynthesis. Additionally, both PBR and PAP7 expression level in the cell lines correlated with their steroidogenic biosynthesis ability, which suggests that PAP7 may be involved in steroid biosynthesis through PBR.

Figure 7:
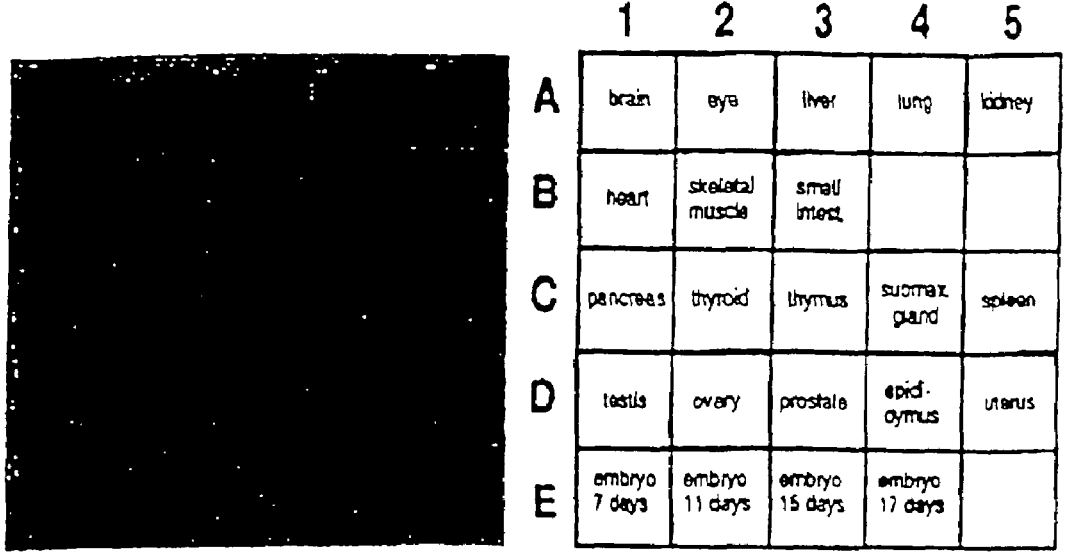
FIG. 7. PAP3 mRNA Tissue distribution analysis by Dot blot analysis. (A), a Master blot containing 100–500 ng of poly(A)+ RNA from mouse tissues were hybridized at high stringency with a $^{32}$P-labeled PAP3 probe as described under "Experimental Procedures." The autoradiogram was exposed overnight. (B), densitometric analysis of PAP3 expression.
Figure 7:
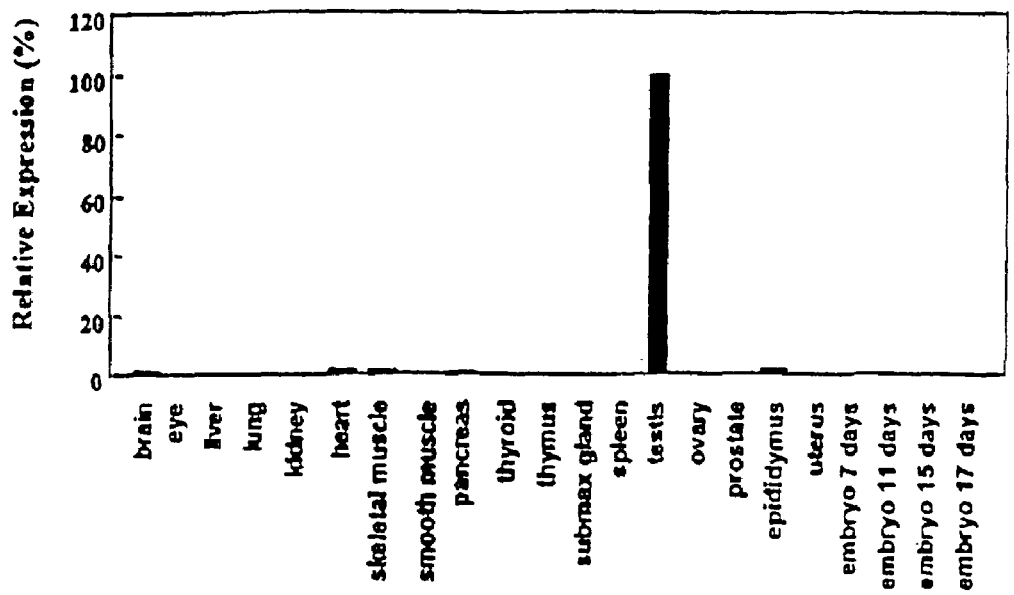
Figure 8:
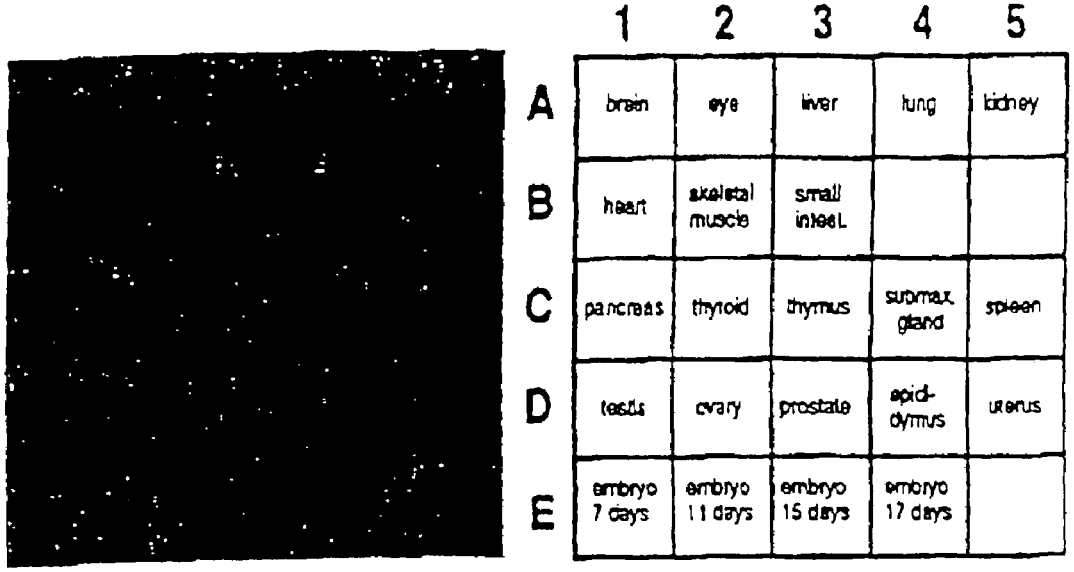
FIG. 8. PAP20 mRNA Tissue distribution analysis by Dot blot analysis. (A), a Master blot containing 100–500 ng of poly(A)+ RNA from mouse tissues were hybridized at high stringency with a $^{32}$P-labeled PAP20 probe as described under "Experimental Procedures." The autoradiogram was exposed overnight. (B), densitometric analysis of PAP20 expression.
Figure 8:
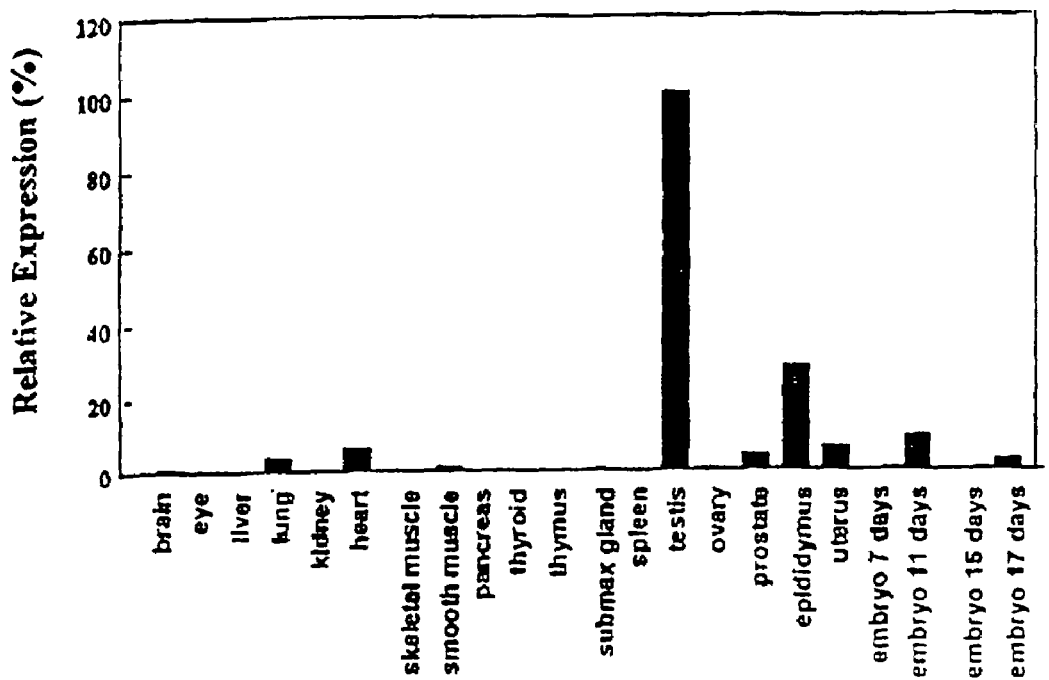

PAP 8, PAP15, and PAP20, are novel genes. The polypeptide encoded by PAP20 has two potential myristoylation sites, one PKC phosphorylation site and one PKA phosphorylation site. Protein myristoylation enables the protein to attach to the cellular membrane and thus take part in cell signaling (Casey, P. J. 1995, Science 268, 221–225; Boutin, J. A. 11997, *Cell Signal* 9, 15–35). PAP20 is predominantly expressed in the testis. Interaction of PBR with PAP20 increased the affinity of ligand binding using PK11195 as a ligand. Therefore, it is likely that PAP20 serves to increase or decrease PBR function by modulating PBR's affinity to its endogenous ligand, DBI. The tissue distribution of PAP3 and PAP20 is shown in FIG. 7 and FIG. 8, respectively.

Thus, one aspect of the invention provides an isolated nucleic acid molecule comprising a polynucleotide having a nucleotide sequence selected from SEQ ID NO:1–9 encoding PAPs polypeptides. It is within the skill of a person with ordinary skill in the art to use the sequences provided herein for the purpose of cloning cDNA or genomic sequences which encode other parts or complete portions of the PAP genes described herein and therefore, these related sequences are encompassed within the present invention.

In addition, isolated nucleic acid molecules of the invention include DNA molecules which comprise a sequence substantially different from those described above but which, due to the degeneracy of the genetic code, still encode PAPs. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli* or plant host).

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the antisense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

The present invention is further directed to nucleic acid molecules encoding portions or fragments of the nucleotide sequences described herein. Fragments include portions of the nucleotide sequences of at least 10 contiguous nucleotides in length selected from any two integers, one of which representing a 5' nucleotide position and a second of which representing a 3' nucleotide position, where the first nucleotide for each nucleotide sequence is position 1. That is, every combination of a 5' and 3' nucleotide position that a fragment at least 10 contiguous nucleotide bases in length or any integer between 10 and the length of an entire nucleotide sequence minus 1.

Further, the invention includes polynucleotides comprising fragments specified by size, in nucleotides, rather than by nucleotide positions. The invention includes any fragment size, in contiguous nucleotides, selected from integers between 1- and the entire length of an entire nucleotide sequence minus 1. Preferred sizes include 20–50 nucleotides, 50–300 nucleotides useful as primers and probes. Regions from which typical sequences may be derived include but are not limited to, for example, regions encoding specific epitopes or domains within said sequence, for example, the PBR binding domain extending in SEQ ID NO:1, 2, 3, 4, and 5, potential myristoylation sites at positions 262–267 and 271–276 of SEQ ID NO:7 and five PKC phosphorylation sites at 395–396, 113–115, 255–257, 280–282, 331–333, and 339–341 of SEQ ID NO:7, an Acyl-Co-A site at position 24–108 of SEQ ID NO:7, a nuclear localization domain at position 150–167 of SEQ ID NO:7, a troponin site at position 98–247 of SEQ ID NO:7 and an HSP90 domain at position 126–155 of SEQ ID NO:7, among others.

In another aspect, the invention provides isolated nucleic acid molecules comprising polynucleotides which hybridize under stringent hybridization conditions to a polynucleotide sequence of the present invention described above, or a specified fragment thereof. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 g/ml denatured sheared salmon sperm DNA, followed by washing the filters in 0.1×SSC at about 65° C.

The sequences encoding the polypeptides of the present invention or portions thereof may be fused to other sequences which provide additional functions known in the art such as a marker sequence, or a sequence encoding a peptide which facilitates purification of the fused polypeptide, peptides having antigenic determinants known to provide helper T-cell stimulation, peptides encoding sites for post-translational modifications, or amino acid sequences which target the fusion protein to a desired location, e.g. a heterologous leader sequence.

The present invention further relates to variants of the nucleic acid molecules of the present invention, which encode portions, analogs or derivatives of the PAPs of the present invention. A variant may occur naturally, such as a natural allelic variant. By an "allelic variant" is intended one of several alternate forms of a gene occupying a given locus of a chromosome of an organism. Non-naturally occuring variants may be produced by known mutagenesis techniques. Such variants include those produced by nucleotide substitution, deletion, or addition of one or more nucleotides in the coding or noncoding regions or both. Alterations in the coding regions may produce conservative or nonconservative amino acid substitutions, deletions, or additions. Especially preferred among these are silent substitutions, additions, and deletions which do not alter the properties and activities of PAPs polypeptides disclosed herein or portions thereof. Also preferred in this regard are conservative substitutions.

Nucleic acid molecules with at least 90–99% identity to a nucleic acid identified above is another aspect of the present invention. These nucleic acids are included irrespective of whether they encode a polypeptide having PAP activity. By "a polypeptide having PAP activity" is intended polypeptides exhibiting activity similar, but not identical, to an activity of the PAP of the invention, as measured in the assays described below. The biological acitivity or function of the polypeptides of the present invention are expected to be similar or identical to polypeptides from other organisms that share a high degree of structural identity/similarity.

In another embodiment, the present invention relates to a recombinant DNA molecule that includes a vector and a DNA sequence as described above. The vector can take the form of a plasmid, phage, cosmid, YAC, eukaryotic expression vector such as a DNA vector, *Pichia pastoris*, or a virus vector such as for example, baculovirus vectors, retroviral vectors or adenoviral vectors, and others known in the art. The cloned gene may optionally be placed under the control of (i.e., operably linked to) certain control sequences such as promoter sequences, or sequences which may be inducible and/or cell type-specific. Suitable promoters will be known to a person with ordinary skill in the art. The expression construct will further contain sites for transcription initiation, termination and, in the transcribed region, a ribosome binding site for translation. Among the vectors preferred for use include pGBT9, PGAD10 (Clonetech), PSVzeo (Invitrogen), pBlueScript (Stratagene), pCMV5 (Invitrogen), pCRII (Invitrogen) to name a few.

Introduction of the construct into the host cell can be effected by calcium phosphate transfection, electroporation, infection, and other methods known in the art and described in standard laboratory manuals such as *Current Protocols in Molecular Biology*, Ausubel, F. M. et al. (Eds), Wiley & Sons, Inc. All documents cited herein supra and infra are hereby incorporated in their entirety by referece thereto.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to rat and human). Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also, contain sequences conferring antibiotic resistance markers. These markers may be used to obtain successful transformants by selection. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods. The DNA sequence can be present in the vector operably linked to a sequence encoding an IgG molecule, an adjuvant, a carrier, or an agent for aid in purification of PAPs, such as glutathione S-transferase, or a series of histidine residues also known as a histidine tag. The recombinant molecule can be suitable for transfecting plant cells or eukaryotic cells, for example, mammalian cells and yeast cells in culture systems. *Saccharomyces cerevisiae*, *Saccharomyces carlsbergensis*, and *Pichia pastoris* are the most commonly used yeast hosts, and are convenient fungal hosts. Control sequences for yeast vectors are known in the art. Mammalian cell lines available as hosts for expression are known in the art and include many immortalized cell lines available from the American Type Culture Collection (ATCC), such as HEK293 cells, and NIH 3T3 cells, MA10 Leydig cells, mouse C6 glioma cells, Y1 adrenal cells, and breast cancer cell lines such as MDA-231, MCF-7, to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences and poly A addition sequences; enhancer sequences which increase expression may also be included, and sequences which cause amplification of the gene may also be desirable. These sequences are known in the art. The transformed or transfected host cells can be used as a source of DNA sequences described above. When the recombinant molecule takes the form of an expression system, the transformed or transfected cells can be used as a source of the protein described below.

In another embodiment, the present invention relates to the PAP polypeptides described above or any allelic variation thereof which is immunologically identifiable with the polypeptides.

A polypeptide or amino acid sequence derived from the amino acid sequences mentioned above, refers to a polypeptide having an amino acid sequence identical to that of a polypeptide encoded in the sequence, or a portion thereof wherein the portion consists of at least 2–5 amino acids, and more preferably at least 8–10 amino acids, and even more preferably at least 11–15 amino acids, or which is immunologically identifiable with a polypeptide encoded in the sequence.

A recombinant or derived polypeptide is not necessarily translated from a designated nucleic acid sequence; it may be generated in any manner, including for example, chemical synthesis, or expression of a recombinant expression system. In addition the polypeptide can be fused to other proteins or polypeptides which increase its antigenicity, such as adjuvants for example.

As noted above, the methods of the present invention are suitable for production of any polypeptide of any length, via insertion of the above-described nucleic acid molecules or vectors into a host cell and expression of the nucleotide sequence encoding the polypeptide of interest by the host cell. Introduction of the nucleic acid molecules or vectors into a host cell to produce a transformed host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986). Once transformed host cells have been obtained, the cells may be cultivated under any physiologically compatible conditions of pH and temperature, in any suitable nutrient medium containing assimilable sources of carbon, nitrogen and essential minerals that support host cell growth. Recombinant polypeptide-producing cultivation conditions will vary according to the type of vector used to transform the host cells. For example, certain expression vectors comprise regulatory regions which require cell growth at certain temperatures, or addition of certain chemicals or inducing agents to the cell growth medium, to initiate the gene expression resulting in the production of the recombinant polypeptide. Thus, the term "recombinant polypeptide-producing conditions," as used herein, is not meant to be limited to any one set of cultivation conditions. Appropriate culture media and conditions for the above-described host cells and vectors are well-known in the art. Following its production in the host cells, the polypeptide of interest may be isolated by several techniques. To liberate the polypeptide of interest from the host cells, the cells are lysed or ruptured. This lysis may be accomplished by contacting the cells with a hypotonic solution, by treatment with a cell wall-disrupting enzyme such as lysozyme, by sonication, by treatment with high pressure, or by a combination of the above methods. Other methods of bacterial cell disruption and lysis that are known to one of ordinary skill may also be used.

Following disruption, the polypeptide may be separated from the cellular debris by any technique suitable for separation of particles in complex mixtures. The polypeptide may then be purified by well known isolation techniques. Suitable techniques for purification include, but are not limited to, ammonium sulfate or ethanol precipitation, acid extraction, electrophoresis, immunoadsorption, anion or cation exchange chromatography, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hydroxylapatite chromatography and lectin chromatography.

The recombinant polypeptide or fusion protein can be used, detectably labeled and unlabeled, as a diagnostic tool for the detection of PAPs or for the detection and measurement of PBR. Additionally, these polypeptides can be used in a method for modulating PBR expression. In addition, the recombinant protein can be used as a therapeutic agent to reduce cell death and/or increase cell proliferation via its effect on PBR function. The transformed host cells can be used to analyze the effectiveness of drugs and agents which modulate PBR function, expression or targeting via their effect on the expression or function of PAPs, such as host proteins or chemically derived agents or other proteins which may interact with the cell to alter the PAP function or expression, thereby modulating PBR function, expression or localization.

In another embodiment, the present invention relates to monoclonal or polyclonal antibodies specific for the above-described recombinant proteins (or polypeptides). For instance, an antibody can be raised against a peptide described above, or against a portion thereof of at least 10 amino acids, perferrably, 11–15 amino acids. Persons with ordinary skill in the art using standard methodology can raise monoclonal and polyclonal antibodies to the protein (or polypeptide) of the present invention, or a unique portion thereof. Material and methods for producing antibodies are well known in the art (see for example Goding, in, *Monoclonal Antibodies: Principles and Practice*, Chapter 4, 1986).

The amount of PAP expression can be detected at several levels. Using standard methodology well known in the art, assays for the detection and quantitation of PAP RNA can be designed, and include northern hybridization assays, in situ hybridization assays, and PCR assays, among others. Please see e.g., Maniatis, Fitsch and Sambrook, *Molecular Cloning; A Laboratory* Manual (1982) or *DNA Cloning*, Volumes I and II (D. N. Glover ed. 1985), or *Current Protocols in Molecular Biology*, Ausubel, F. M. et al. (Eds), Wiley & Sons, Inc. for general description of methods for nucleic acid hybridization. Polynucleotide probes for the detection of PAP RNA can be designed from the sequences described in SEQ ID NO: 1–9. For example, RNA isolated from samples can be coated onto a surface such as a nitrocellulose membrane and prepared for northern hybridization. In the case of in situ hybridization of biopsy samples for example, the tissue sample can be prepared for hybridization by standard methods known in the art and hybridized with polynucleotide sequences which specifically recognize PAP RNA. The presence of a hybrid formed between the sample RNA and the polynucleotide can be detected by any method known in the art such as radiochemistry, or immunochemistry, to name a few.

One of skill in the art may find it desirable to prepare probes that are fairly long and/or encompass regions of the amino acid sequence which would have a high degree of redundancy in the corresponding nucleic acid sequences. In other cases, it may be desirable to use two sets of probes simultaneously, each to a different region of the gene. While the exact length of any probe employed is not critical, typical probe sequences are no greater than 500 nucleotides, even more typically they are no greater than 250 nucleotides; they may be no greater than 100 nucleotides, and also may be no greater than 75 nucleotides in length. Longer probe sequences may be necessary to encompass unique polynucleotide regions with differences sufficient to allow related target sequences to be distinguished. For this reason, probes are preferably from about 10 to about 100 nucleotides in length and more preferably from about 20 to about 50 nucleotides.

The DNA sequence of PAPs can be used to design primers for use in the detection of PAPs using the polymerase chain reaction (PCR) or reverse transcription PCR (RT-PCR). The primers can specifically bind to the PAP cDNA produced by reverse transcription of PAP RNA, for the purpose of detecting the presence, absence, or quantifying the amount of PAP by comparison to a standard. The primers can be any length ranging from 7–40 nucleotides, preferably 10–15 nucleotides, most preferably 18–25 nucleotides homologous or complementary to a region of the PAP sequence. Reagents and controls necessary for PCR or RT-PCR reactions are well known in the art. The amplified products can then be analyzed for the presence or absence of PAP sequences, for example by gel fractionation, by radiochemistry, and immunochemical techniques. This method is advantageous since it requires a small number of cells. Once PAP is detected, a determination whether the cell is overexpressing or underexpressin PAP can be made by comparison to the results obtained from a normal cell using the same method. For example, increased PAP7 RNA levels correlate with PBR expression levels, especially in steroidogenic cells, wherein, an increase in steroidogenic capability of the cells correlates with an increase in PBR and PAP7 RNA.

In another embodiment, the present invention relates to a diagnostic kit for the detection of PAP RNA in cells, said kit comprising a package unit having one or more containers of PAP oligonucleotide primers for detection of PAP by PCR or RT-PCR or PAP polynucleotides for the detection of PAP RNA in cells by in situ hybridization or northern analysis, and in some kits including containers of various reagents used for the method desired. The kit may also contain one or more of the following items: polymerization enzymes, buffers, instructions, controls, detection labels. Kits may include containers of reagents mixed together in suitable proportions for performing the methods in accordance with the invention. Reagent containers preferably contain reagents in unit quantities that obviate measuring steps when performing the subject methods.

In a further embodiment, the present invention provides a method for identifying and quantifying the level of PAP present in a particular biological sample. Any of a variety of methods which are capable of identifying (or quantifying) the level of PAP in a sample can be used for this purpose.

Diagnostic assays to detect PAPs may comprise a biopsy or in situ assay of cells from an organ or tissue sections, as well as an aspirate of cells from a tumor or normal tissue. In addition, assays may be conducted upon cellular extracts from organs, tissues, cells, urine, or serum or blood or any other body fluid or extract.

When assaying a biopsy, the assay will comprise, contacting the sample to be assayed with a PAP ligand, natural or synthetic, or an antibody, polyclonal or monoclonal, which recognizes PAP, or antiserum capable of detecting PAP, and detecting the complex formed between PAP present in the sample and the PAP ligand or antibody added.

PAP ligands or substrates include for example, PBR, in addition to natural and synthetic classes of ligands and their derivatives which can be derived from natural sources such as animal or plant extracts.

PAP ligands or anti-PAP antibodies, or fragments of ligand and antibodies capable of detecting PAP may be labeled using any of a variety of labels and methods of labeling for use in diagnosis and prognosis of disease associated with increased cell proliferation, such as cancer, or reduced cell death. Examples of types of labels which can be used in the present invention include, but are not limited to, enzyme labels, radioisotopic labels, non-radioactive isotopic labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^{3}$H, $^{111}$In, $^{125}$I, $^{32}$P, $^{35}$S, 14C, $^{57}$To, $^{58}$Co, $^{59}$Fe, $^{75}$Se, $^{152}$Eu, $^{90}$Y, $^{67}$Cu, $^{21}$Ci, $^{211}$A, $^{212}$Pb, $^{47}$Sc, $^{109}$Pd, $^{11}$C, $^{19}$F, $^{123}$I, etc.

Examples of suitable non-radioactive isotopic labels include $^{157}$Gd, $^{55}$Mn, $^{162}$Dy, $^{52}$Tr, $^{46}$Fe, etc.

Examples of suitable fluorescent labels include a $^{152}$Eu label, a fluorescein label, an isothiocyanate label, a rhodamine label, a phycoerythrin label, a phycodyanin label, an allophycocyanin label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, etc.

Those of ordinary skill in the art will know of other suitable labels which may be employed in accordance with the present invention. The binding of these labels to ligands and to antibodies or fragments thereof can be accomplished using standard techniques commonly known to those of ordinary skill in the art. Typical techniques are described by Kennedy, J. H., et al., 1976 (*Clin. Chim. Acta* 70:1–31), and Schurs, A. H. W. M., et al. 1977 (*Clin. Chim Acta* 81:1–40). Coupling techniques mentioned in the latter are the glutaraldehyde method, the periodate method, the dimaleimide method, and others, all of which are incorporated by reference herein.

The detection of antibodies (or fragments of antibodies) of the present invention can be improved through the use of carriers. Well-known carriers include glass, polystyrene, polypropylene, polyethylene, dextran, nylon, amylases, natural and =modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to PAP. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.

The ligands or antibodies, or fragments of antibodies or ligands of PAPs discussed above may be used to quantitatively or qualitatively detect the presence of PAP. Such detection may be accomplished using any of a variety of immunoassays known to persons of ordinary skill in the art such as radioimmunoassays, immunometic assays, etc. Using standard methodology well known in the art, a diagnostic assay can be constructed by coating on a surface (i.e. a solid support) for example, a microtitration plate or a membrane (e.g. nitrocelluolose membrane), antibodies specific for PAP or a portion of PAP, and contacting it with a sample from a person suspected of having a PAP related disease. The presence of a resulting complex formed between PAP in the sample and antibodies specific therefor can be detected by any of the known detection methods common in the art such as fluorescent antibody spectroscopy or colorimetry. A good description of a radioimmune assay may be found in *Laboratory Techniques and Biochemistry in Molecular Biology*. by Work, T. S., et al. North Holland Publishing Company, N.Y. (1978), incorporated by reference herein. Sandwich assays are described by Wide at pages 199–206 of *Radioimmune Assay Method*, edited by Kirkham and Hunter, E. & S. Livingstone, Edinburgh, 1970.

The diagnostic methods of this invention can be predictive of diseases involving PBR including gallstones, atherosclerosis, Niemann-Pick C, Sitosterolemia, Dystrophy, Tumor proliferation (tumorigenesis), Schnyder's corneal crystalline dystrophy. Brain disorders include cholesterol metabolism and Alzheimer's disease, Tellurium toxicity, Smith-Lemli-Opitz syndrome, myelinization, developmental abnormalities and demyelization: Charcot-Marie-Tooth disease; Pelizaeus-Merzbacher disease, Multiple sclerosis, SLA, to name a few. Alternatively, the methods and compositions may be useful as prophylactic treatment, or in screening for compounds effective in prophylactic treatments.

The recombinant protein can be used to identify inhibitors or activators of a PAP activity which allows the identification of drugs or agents which modulate PBR activity. Using an assay as described below in the Examples, or for example, introducing a drug or agent to a cell expressing a PAP and detecting a increase or decrease in the level of PAP RNA or protein, natural and synthetic agents and drugs can be discovered which result in a reduction or elimination, or increase in a PAP activity. Knowledge of the mechanism of action of the inhibitor or activator is not necessary as long as a decrease or increase in the activity of a PAP is detected. Inhibitors may include agents or drugs which either bind or sequester the PAP's substrate(s), such as PBR, or cofactor(s), or inhibit PAP itself, directly, for example by irreversible binding of the agent or drug to the PAP, or indirectly, for example by introducing an agent which binds the competes with PAP binding to its substrate. Activators may include cofactors necessary for proper PAP function or agents which allow a higher turnover rate of binding or release of the PAP to/from PBR or the particular PAP substrate. Agents or drugs related to this invention may result in partial or complete inhibition or various degrees of activation of PAP which may or may not result in modulation of PBR function. Inhibitors or activators of PAP activity may be used in the treatment or amelioration of conditions such as stress, cancer, neurodegenerative disorders, i.e. stroke, Alzheimer's, developmental disorders, infertility, and immune disorders.

Agents which decrease the level of PAP (i.e. in a human or an animal) or reduce or inhibit PAP activity may be used in the therapy of any disease associated with the elevated levels of PAP. Similarly, agents which increase the level of PAP or activate PAP activity may be used in the therapy of any disease associated with reduced levels of PAP. An increase or decrease in the level of PAP is determined when the change in the level of PAP is about 2–3 fold higher or lower than the level of PAP in the normal cell, up to about 10–100 fold higher or lower than the amount of PAP in a normal cell. Agents which decrease PAP RNA include, but are not limited to, one or more ribozymes capable of digesting PAP RNA, or antisense oligonucleotides capable of hybridizing to PAP RNA such that the translation of PAP is inhibited or reduced resulting in a decrease in the level of PAP. These agents can be administered as DNA, as DNA entrapped in proteoliposomes containing viral envelope receptor proteins (Kanoda, Y. et al., 1989, *Science* 243, 375) or as part of a vector which can be expressed in the target cell such that the DNA or RNA is made. Vectors which are expressed in particular cell types are known in the art, for example, for the mammary gland, please see Furth, (1997) (*J. Mammary Gland Biol. Neopl.* 2, 373) for examples of conditional control of gene expression in the mammary gland. Alternatively, the DNA can be injected along with a carrier. A carrier can be a protein such as a cytokine, for example interleukin 2, or polylysine-glycoprotein carrier. Such carrier proteins and vectors and methods of using same are known in the art. In addition, the DNA could be coated onto tiny gold beads and said beads introduced into the skin with, for example, a gene gun (Ulmer, J. B. et al., 1993, *Science* 259, 1745).

Alternatively, antibodies, or compounds capable of reducing or inhibiting PAP activity, that is reducing or inhibiting either the expression, production or activity of PAP, such as antagonists, can be provided as an isolated and substantially purified protein, or as part of an expression vector capable of being expressed in the target cell such that the PAP-reducing or inhibiting agent is produced. Similarly, compounds capable of increasing or activating PAP activity, that is increasing or activating either the expression, production, or activity of PAP, such as agonists, can be provided as an isolated and substaially purified protein, or as part of an expression vector capable of being expressed in the target cell such that the PAP-elevating or activating agent is produced. In addition, factors which affect the stability of the protein, and co-factors such as various ions, i.e. Ca2+ (Calvo, D. J. and Medina, J. H., 1993, *J. Recept. Res.* 13:975–987), or anions, such as halides or anion channel blockers such as DIDS (4,4,diisothiocyanostilbene-2,2'-disulfonic acid), an ion transport blocker (Skolnick, P., 1987, *Eur. J. Pharmacol.* 133:205–214), or factors which affect the stability of PBR such as lipids, for example, the phospholipids phosphatidylserine and phosphatidylinositol whereby the presence of the phospholipids is required for receptor activity (Moynagh, P. N. and Williams, D. C., 1992, *Biochem. Pharmacol.* 43:1939–1945) can be administered to modulate the expression and function of the PAPs and PBR. These formulations can be administered by standard routes. In general, the combinations may be administered by the topical, transdermal, intraperitoneal, oral, rectal, or parenteral (e.g. intravenous, subcutaneous, or intramuscular) route. In addition, PAP-inhibiting or PAP-activating compounds may be incorporated into biodegradable polymers being implanted in the vicinity of where drug delivery is desired, for example, at the site of a tumor or implanted so that the PAP-inhibiting or PAP-activating compound is slowly released systemically. The biodegradable polymers and their use are described, for example, in detail in Brem et al. (1991) *J. Neurosurg.* 74, 441–446. These compounds are intended to be provided to recipient subjects in an amount sufficient to effect the inhibition of PAP. Similarly, agents which are capable of negatively or positively effecting the expression, production, stability or function of PAP, are intended to be provided to recipient subjects in an amount sufficient to result in the desired effect. An amount is said to be sufficient to "effect" the inhibition or induction of PAP if the dosage, route of administration, etc. of the agent are sufficient to influence such a response.

The PAPs identified in this application were discovered due to their ability to associate with PBR, and may play a role in the proper targeting, function, expression, or stability of PBR. Therefore, a method for inhibiting or reducing PBR function, or altering the localization of PBR, would include a method for dissociating PAPs from the receptor. This is possible using agents which block the site on PBR at which these PAPs associate with PBR, or alternatively, blocking the site on the PAPs which is involved in PBR-association. Such agents would include antibodies or antagonists which recognize such sites or which alter the conformation of these sites such that PAP and PBR association is inhibited or eliminated. Agents which decrease the level of PBR (i.e. in a human or an animal) or reduce or inhibit PBR activity may be used in the therapy of any disease associated with the elevated levels of PBR such as metastatic cancer, for example breast cancer, or diseases associated with increased cell proliferation or increased cholesterol transport into the cell. An increase in the level of PBR is determined when the level of PBR in a tumor cell is about 2–3 times the level of PBR in the normal cell, up to about 10–100 times the amount of PBR in a normal cell.

Antibodies or compounds capable of reducing or inhibiting the association between PBR and PAPs can be provided as an isolated and substantially purified protein, or as part of an expression vector capable of being expressed in the target cell such that the PBR-PAP-association reducing or inhibiting agent is produced. These formulations can be administered by standard routes. In general, the combinations may be administered by the topical, transdermal, intraperitoneal, oral, rectal, or parenteral (e.g. intravenous, subcutaneous, or intramuscular) route. In addition, these compounds may be incorporated into biodegradable polymers being implanted in the vicinity of where drug delivery is desired, for example, at the site of a tumor or implanted so that the compound is slowly released systemically. The biodegradable polymers and their use are described, for example, in detail in Brem et al. (1991) *J. Neurosurg.* 74, 441–446.

These compounds are intended to be provided to recipient subjects in an amount sufficient to effect the inhibition of PBR/PAP association.

In line with the function of PBR in cell proliferation, agents which stimulate the function of PBR by increasing the association of PAPs to PBR, may be used in the therapy of any disease associated with a decrease of PBR, or a decrease in cell proliferation, wherein PBR is capable of increasing such proliferation, e.g. developmental retardation. PBR has also been shown to be involved in cholesterol transport, therefore, an agent or drug which results in an increase in function or stability of PBR and its associated PAPs can be used to increase cholesterol transport into cells. Diseases where cholesterol transport is defficient include lipoidal adrenal hyperplasia, and diseases where there is a requirement for increased production of compounds requiring cholesterol such as myelin and myelination including Alzheimer's disease, spinal chord injury, and brain development neuropathy [Snipes, G. and Suter, U. (1997) Cholesterol and Myelin. In: *Subcellular Biochemistry*, Robert Bittman (ed.), vol. 28, pp. 173–204, Plenum Press, New York], to name a few.

In providing a patient with any agent which modulates the expression, function, targeting, or association of PAP or PBR as discussed above, the dosage of administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient), although a lower or higher dosage may be administered.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* [16th ed., Osol, A. ed., Mack Easton Pa. (1980)]. In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

The present invention also provides kits for use in the diagnostic or therapeutic methods described above. Kits according to this aspect of the invention may comprise one or more containers, such as vials, tubes, ampules, bottles and the like, which may comprise one or more of the compositions of the invention.

The kits of the invention may comprise one or more of the following components, one or more compounds or compositions of the invention, and one or more excipient, diluent, or adjuvant.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention. The following Materials and Methods were used in the Examples desribed below.

MATERIAL AND METHODS

Materials $[\alpha\text{-}^{32}P]$dCTP (specific actifity, 3000 Ci/mmol), [1,2,6,7-N-3H]progesterone (specific activity, 94.1 Ci/mmol) and $^3$H-1-(2-chlorophenyl)-N-methyl-N-(1-methyl-propyl)-3-isoquinolinecarboxamide (PK 11195) (specific activity, 86.9 Ci/mmol) were obtained from NEN Life Science Products (Boston, Mass.). PK11195 was obtained from Research Biochemicals, Inc. (Natick, Mass.). Nitrocellulose (0.45 μm) was from Hoeffer Scientific (San Francisco, Calif.). 22R Hydroxycholesterol was purchased from Sigma. Restriction enzymes were from Stratagene (La Jolla, Calif.) and New England Biolabs (Beverly, Mass.). Cell culture supplies were purchased from from Life Technologies, Inc. (Grand Island, N.Y.). Tissue culture plasticware was from Corning (Corning, N.Y.). Electrophoresis reagents and materials were supplied from BioRad. All other chemicals used were of analytical grade and were obtained from various commercial sources.

Strains and Media

The genotype of the *Saccharomyces cerevisiae* reporter strain HF7c is MATa, ura3–52, his3–200, lys2–801, ade2–101, trp1–901, leu2–3, 112, gal4–542, gal80–538, LYS2::GAL-HIS3, URA3:: (GAL4 17-mers)$_3$-CYC1-lacZ (CLONTECH, Palo Alto, Calif.). Yeast strains were grown at 30° C. in standard liquid YPD medium or minimal SD synthetic medium with appropriate supplement amino acids (CLONTECH, Palo Alto, Calif.).

Plasmids and Construction

The mouse PBR cDNA coding sequence was subcloned into pGBT9 (CLONTECH, Palo Alto, Calif.) at EcoR I and BamH I sites (pGBT-PBR). The fusion site was verified by sequencing. Functional fusion PBR protein, expressed in yeast cells, was verified by PBR ligand binding assay. Mouse testis cDNA library was constructed in pGAD10 [LEU2, GAL4 (768–881)] (CLONTECH, Palo Alto, Calif.). Amplification of premade libraries was performed by growing the transformants on LB-agar-ampicillin and purifying the plasmids DNA with QIAGEN Plasmid Giga kit (QIAGEN, Valencia, Calif.). In the transfection experiments, PAP7 partial sequence (including 192 Amino acids C-terminal sequence) was inserted into pSVzeo vector (In-vitrogen, Carlsbad Calif.) at EcoRI and BamH1 sites.

Yeast Two-Hybrid Screening

The Clontech MATCHMAKER two-hybrid system was applied in this study (detailed in manufacturer's instruction book). Briefly, the yeast reporter host strain HF7c was simultaneously cotransformed with both pGBT-PBR and the mouse testis cDNA library in pGAD10 plasmid by using lithium acetate high-efficiency method (Gietz, D. et al., 1992, *Nucleic Acids Res.* 20, 1425). HIS positive clones were further selected by colony lift filter assay for β-galactosidase activity. Plasmid DNA was rescued in *Escherichia coli* DH5? from yeast cells. Plasmids were retransformed into yeast HF7c cells with plasmid pGBT-PBR to test for histidine prototrophy and β-galactosidase activity (Clontech manual). The cDNA inserts from the positive clones were sequenced. The full length PAP7 cDNA was obtained by using 5' and 3' RACE kit from kit (CLONTECH, Palo Alto, Calif.).

Sequence Analysis

The ABI PRISM™ dyes terminator cycle sequencing ready reaction kit (PE Biosystems, Foster City, Calif.) and an Applied Biosystems sequencer were used for sequencing (Applied Biosystems, Foster City, Calif.) at the Lombardi Cancer Center Sequencing Core Facility (Georgetown Unviersity). DNA sequences were analyzed by using Entrez and BLAST program against GeneBank™ Database.

Cell Culture Transient Transfection

MA-10 cells were grown in modified Waymouth's MB752/1 medium containing 15% horse serum, as described previously (Papadopoulos, V. et al., 1990, *J. Biol. Chem.* 265, 3772–3779). Mouse C6 glioma and mouse Y1 adrenal cortical cells were cultured in DMEM and DMEM F12 repectively, with 10% fetal bovine serum. MA10 cells were transiently transfected by electroporation (El Hefnawy, T. et al., 1996, *Mol. Cell Endocrinol.* 119, 207–217). Each Genepulser cuvette (0.4 cm-gap, BioRad, Hercules, Calif.) contained 8×10$^6$ cells in 350 μl antibiotic-free complete Waymouth's growth medium (see above), plus 30 μg plasmids DNA in 50 μl of 0.1×TE. Cells in electroporation cuvettes were electro-shocked at 330 V and at a capacitance of 950 μFd generated from Genepulser (BioRad, Hercules, Calif.). The cells were kept immediately on ice for 10 min before plated into 96 well plates.

Radioligand Binding Assays $^3$H-1-(2-chlorophenyl)-N-methyl-N-(1-methyl-propyl)-3-isoquinolinecarboxamide (PK 11195) (NEN, Boston, Mass.) binding studies were performed as we previously described (Papadopoulos, V. et al., 1990, supra; Garnier, M. et al., 1994, *Molecular Pharmacology* 45, 201–211). The dissociation constant (Kd) and the number of binding sites (Bmax) were determined by Scatchard plot analysis of the data using the LIGAND program (Munson, P. J. and Rodbard, D., 1980, *Anal. Biochem.* 107, 220–239).

RNA (Northern) Blot Analysis

Total tissue and cellular RNA was isolated by the acid guanidinium thiocyanate-phenol-chloroform extraction method using RNA STAT60 reagent (Tel-Test Inc., Friendswood, Tex.). RNA was separated by denature electrophoresis and transfered to Nytran membrane (Schleicher & Schuell Inc., Keene, N.H.). The RNA blots were hybridized with $^{32}$P labeled PAP7 cDNA probe generated from random priming (Boehringer Mannheim, Indianapolis, Ind.). Autoradiography was performed by exposing Kodak X-Omat AR films (Eastman Kodak, Rochester, N.Y.) to the blots at –80° C. overnight.

Steroid Biosynthesis

MA-10 cells were plated into 96-well plate at the density of 2.5×10$^4$/well for overnight. The cells were stimulated with 50 ng/ml hCG in 0.2 ml/well serum-free medium for 2 hours. The culture medium was collected and tested for progesterone production by RIA. The assay was carried out by using anti-progesterone antisera (ICN, Costa Mesa, Calif.), following the conditions recommended by the manufacturer. The progesterone production was normalized by the amount of protein in each well. Radioimmunoassay data was analyzed using the software provided by Wallac (EG&G Wallac, Gaithersburg, Md.).

Antibody Generation and Western Analysis

Rabbit anti-PAP7-antibody was prepared by sequential immunization with a peptide SSDEEEEEEENVT-CEEKAKKNANKP (SEQ ID NO:11) of PAP7 protein, which was coupled to KLH. PAP7 antibodies were purified by an affinity resin containing the same peptide immobilized onto agarose (Bethyl Laboratories, Montgomery, Tex.). MA10 cells were solubilized in sample buffer (25 mM Tris-HCl (pH6.8), 1% SDS, 5% β-mercaptoethanol, 1 mM EDTA, 4% glycerol, and 0.01% bromophenol blue), boiled for 5 min, and loaded onto a 15% SDS-PAGE minigel (MiniProtein II System, BioRad, Richmond, Calif.). Electrophoresis was performed at 25 mA/gel using a standard SDS-PAGE running buffer (25 mM Tris, 192 mM glycine, and 0.1% SDS). The proteins were electrophoretically transferred to nitrocellulose membrane (Schleicher & Schuell Inc., Keene, N.H.). The membrane was incubated in blocking buffer (TTBS buffer (20 mM Tris/HCl, pH 7.5, 0.5M NaCl, and 0.05% Tween-20) containing 10% Carnation nonfat milk) at room temperature for 1 hour, followed by incubation with a primary antibody against PAP7 (1:2000) for 2 hours. The membrane was washed with TTBS three times for 10 min each time. After one-hour incubation with the secondary antibody, goat anti-rabbit IgG conjugated with HRP (Signal Transduction), the membrane was washed with TTBS three times for 10 min each time. Specific protein bands were detected by chemiluminescence using the Renaissance Kit (DuPont-New England Nuclear, Wilmington, Del.) according to manufacturer's directions.

Immunocytochemistry

MA-10 cells were cultured on four-chambered SuperCell Culture Slides (Fisher Scientific, Pittsburgh, Pa.) and fixed with methanol at 4° C. for 15 min. The fixed cells were incubated with PAP7 antibody (1:250 dilution) with or without PAP7 peptide for 1 hour. After washing, the cells were incubated with HRP conjugated goat anti-rabbit secondary antibody (Transduction Lab, Lexington, Ky.) for 1 hour. PAP7 staining was visualized with peroxidase using AEC (3-amino-9-ethyl carbazole) as a chromogen to yield a red reaction product. After counterstaining with hematoxylin, slides were dehydrated and permanently mounted.

Immunohistochemistry

Mouse tissues were freshly snapped in liquid nitrogen. Specimens were fixed in cold methanol right after sectioning for 5 min. The slides were then placed in a chamber containing 0.3% $H_2O_2$ solution in methanol for 20 min at room temperature to inhibit the endogenous peroxidase activity and then incubated in blocking solution (10% goat serum) (Zymed, South San Francisco, Calif.) for 15 min. Subsequently, the slides were incubated with anti-PAP7 antibody (1:250) for 2 h at room temperature, washed with water and PBS, incubated with HRP conjugated goat anti-rabbit secondary antibody for 1 hour at room temperature, and then washed with PBS. After treatment with AEC reagent for 1 hr at 37° C. for color staining, the sections were counterstained with hematoxylin, dehydrated and permanently mounted.

Protein Quantification ans Statistical Analysis

Proteins were quantified by dye-binding assay of Bradford (Bradford, M. M., 1976, *Anal. Biochem.* 72, 248–254) with bovine serum albumin as the standard. Statistical analysis was performed by ANOVA followed by the Student-Newman-Keuls test or the Dunnett multiple comparisons test using the Instat (v.2.04) package from GraphPad, Inc. (San Diego, Calif.).

EXAMPLE 1

Isolation of PBR Associated Proteins

We have used the MATCHMAKER Two-Hybrid System from CLONTECH in order to clone genes whose products interact with PBR protein. GAL4 (1–147)—PBR fusion (plasmid pGBT9+PBR) was used as a bait to screen a mouse MATCHMAKER testis cDNA library constructed into the pGAD10 two-hybrid vector. About $3\times10^6$ transformants were tested, and five positive clones were obtained for their ability to interact with PBR.

Library plasmids from these transformants were rescued in *E. coli* strain DH5α. Both the His+ phenotype and the expression of β-galactosidase were confirmed by a second-round transformation of strain HF7c carrying pGBT9-PBR (Table 1).

TABLE 1

Summary of yeast two hybrid screen of mouse testis library by PBR

| Clone activity | His3 | β-Galactosidase |
| --- | --- | --- |
| PAP3 | + | ++ |
| PAP7 | + | ++ |
| PAP20 | + | ++ |
| Positive control | + | +++ |

Plasmids from these positive clones were first analyzed by restriction enzyme digestion and followed by sequence analysis. Two clones were shown to be coded by single gene, which was an unknown gene and was named as PBR associated protein 7 (PAP7). The other three clones encoded different products. After 5' RACE and 3' RACE, PAP7 cDNA clone was completely sequenced on both strands (SEQ ID NO:2) and it encoded a 463-amino acid protein with a calculated molecular weight of about 52 kDa. A homology search in the Genebank database using the BLAST program showed that this is a new sequence, previously unidentified.

EXAMPLE 2

PAP7 Protein Expression in MA-10 Leydig Tumor Cells

The total MA-10 cell protein extracts were analyzed by western blot using PAP7 antibody. This antibody specifically recognizes a 50 kDa-protein band (FIG. 1A). The PAP7 protein expression in MA-10 cell was also checked by immunocytochemistry. PAP7 antibody specifically stained MA-10 cell, with the signal mostly localized in the cytoplasm (FIG. 1B). This signal can be neutralized by PAP7 peptide, which was used to generate and purify this antibody.

EXAMPLE 3

PAP7 Cells and Tissue Expression by Dot and Northern Blot

Figure 2:
FIG. 2. PAP7 mRNA Tissue distribution analysis by Dot blot analysis. (A), a Master blot containing 100–500 ng of poly(A)+ RNA from mouse tissues were hybridized at high stringency with a $^{32}$P-labeled PAP7 probe as described under "Materials and Methods." The autoradiogram was exposed overnight. (B), densitometric analysis of PAP7 expression.
Figure 2:
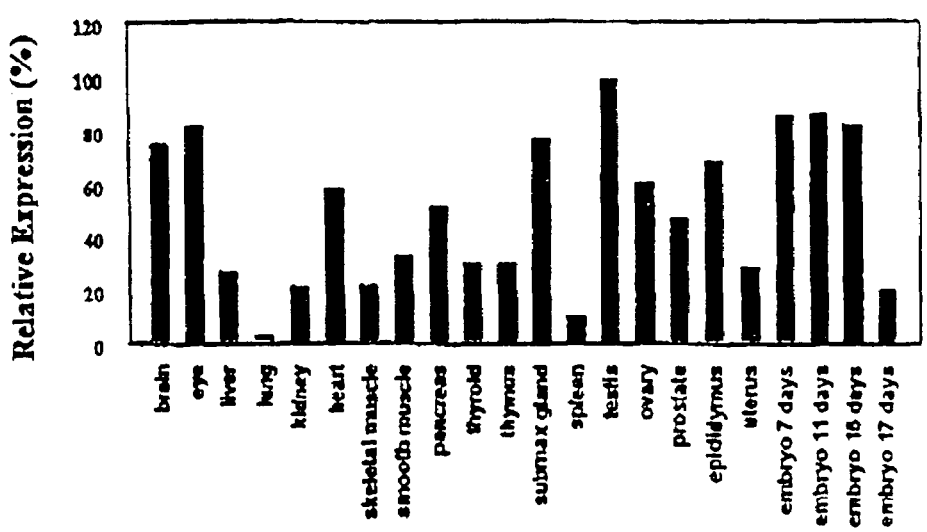
Figure 3:
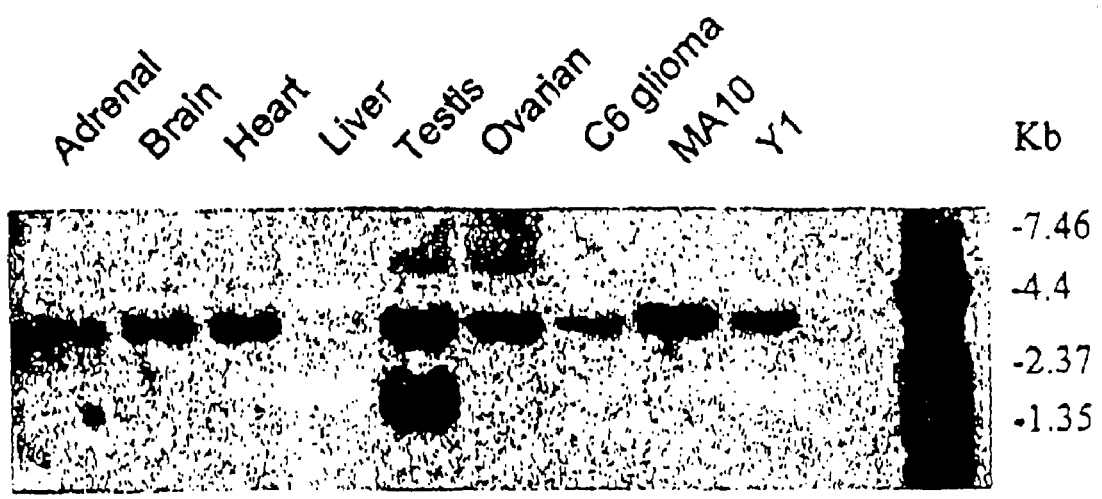
FIG. 3. PAP7 tissue distribution analysis by Northern blot analysis. (A), Northern blot analysis was performed using 20 μg of total RNA/lane from different mouse tissues as indicated. The blot was hybridized at high stringency with a $^{32}$P-labeled PAP7 probe as described under "Materials and Methods". The autoradiogram was exposed overnight. (B), Densitometric analysis of PAP7 expression.
Figure 3:
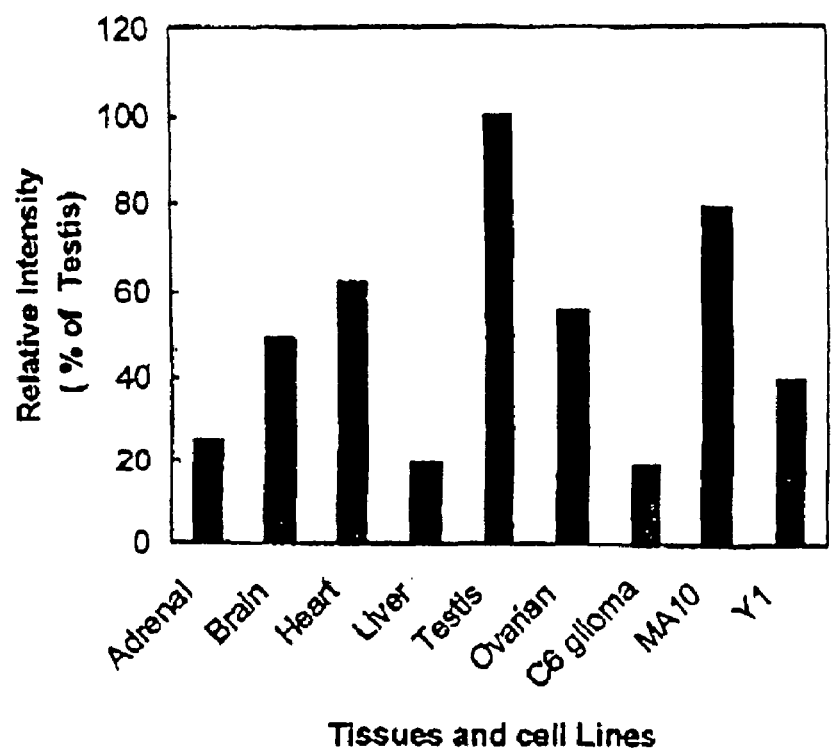
Figure 4:
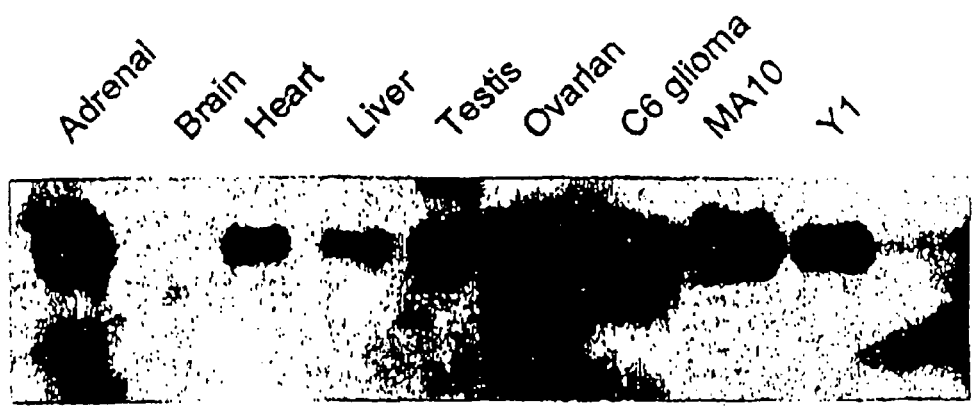
FIG. 4. PBR tissue distribution analysis by Northern blot analysis. (A), Northern blot analysis was performed using 20 μg of total RNA/lane from different mouse tissues as indicated. The blot was hybridized at high stringency with a $^{32}$P-labeled PBR probe as described under "Materials and Methods". The autoradiogram was exposed overnight. (B), For Northern blot analysis, blots were quantitated by densitometry.
Figure 4:
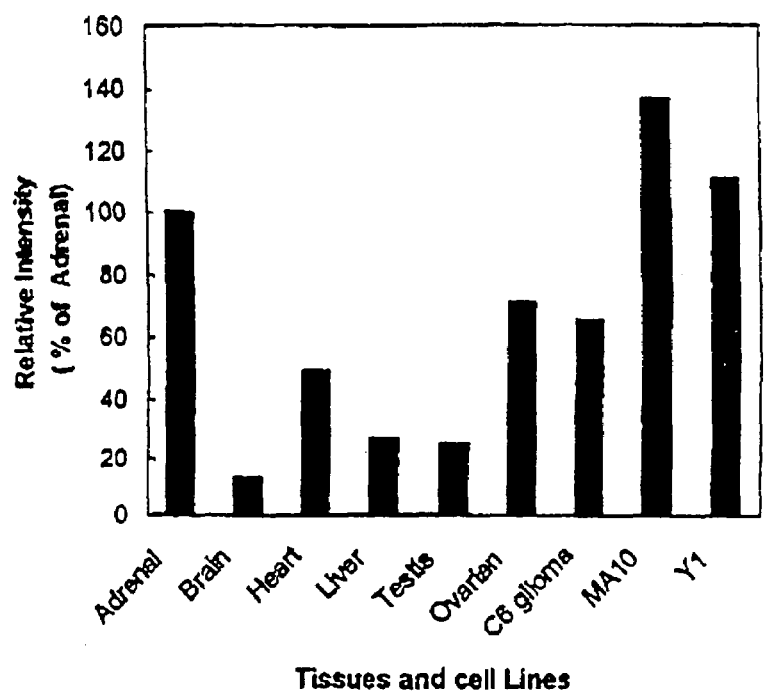

By dot bot analysis, PAP7 was observed to be highly expressed in brain, eye, submax gland, testis, and ovary. Interestingly, PAP7 expression was at its highest level at early embryonic stage, and decreased before birth (FIGS. 2A and 2B). Consistently, PAP7 mRNA was expressed in adrenal, brain, heart, liver, testis and ovarian tissues by Northern blot analysis. PAP7 had a 1 kb transcript which was only expressed in testis and a 3 Kb major mRNA transcript in the other tissues (FIGS. 3A and 3B). PAP7 was also highly expressed in three cell lines, C6 glioma, MA-10 Leydig cells and Y1 adrenal cells, which have been widely used for studying steroid biosynthesis. All three cell lines expressed PAP7 transcript of the same molecular weight size as in normal tissues. The PAP7 expression level in these cell lines was proportionally correlated with their steroidogenic capability (FIGS. 3A and 3B). The PBR mRNA expression level was also checked in these same tissues and cell lines. The PBR expression level was parallel with PAP7 mRNA expression pattern, especially in those three cell lines (FIGS. 4A and 4B).

EXAMPLE 4

PAP7 Cellular Distribution

Figure 5:
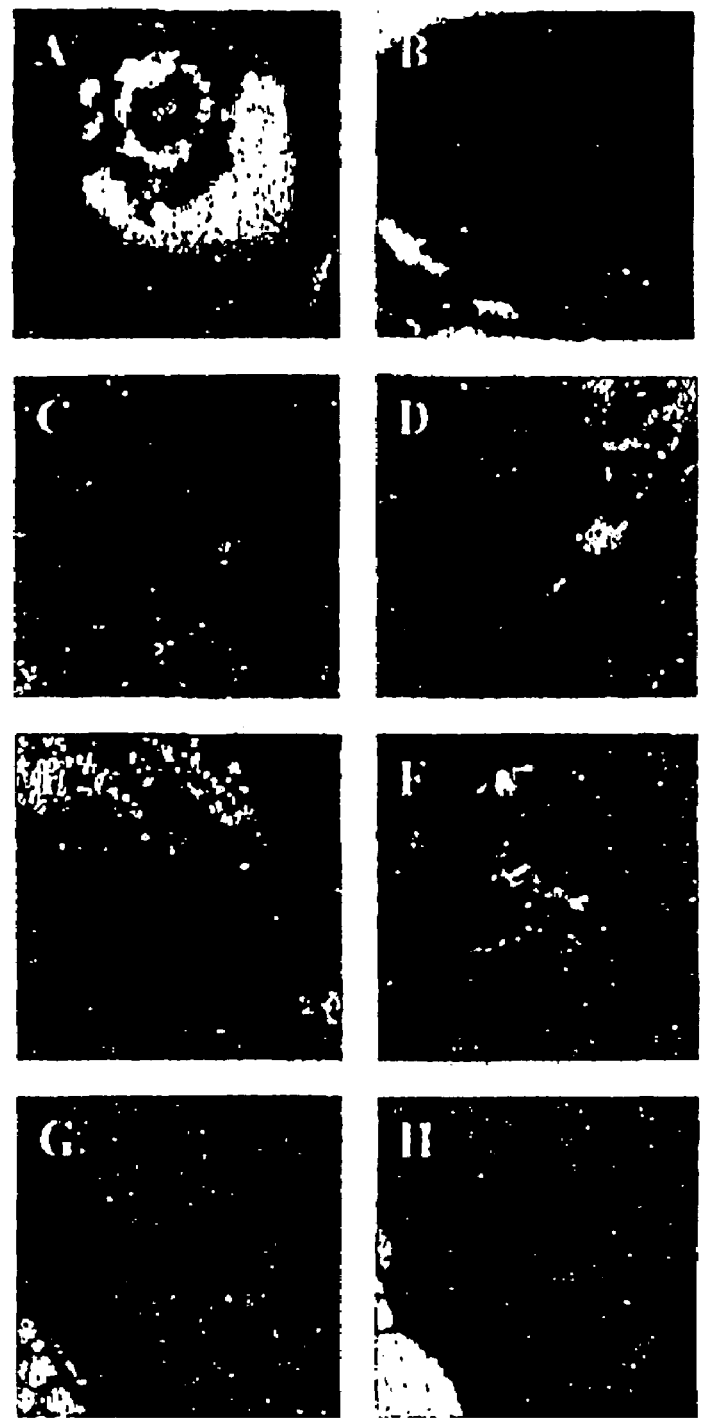
FIG. 5. Immunohistological staining of mouse tissues with anti-PAP-7 antibody. Using anti-PAP-7 antibody to screen various mouse tissues and cells. PAP-7 was present in the granulose cells of the ovary (A and B), in both the Leydig and germ cells of the testis (C and D), in the hippocampus and neuronal cells of the brain (E and F), and the fasciculus cells of the adrenal gland (G and H).

PAP7 protein expression in different tissues was checked by immunohistochemistry (FIG. 5). PAP7 was present in both Leydig and germ cells in testis (FIGS. 5C and 5D), in hypocampus and neuronal cells in brain (FIGS. 5E and 5F), in fasciculata cells in adrenal gland (FIGS. 5G and 5H), and in granulosa cells in ovary (FIGS. 5A and 5B). Liver and kidney expressed low level of PAP7 protein (data not shown) Each specimen was stained with PAP7 peptide neutralized antibody as a negative control. Subsequent in situ hybridization studies showed that PAP7 mRNA followed PAP-7 protein expression.

EXAMPLE 5

The Effect of PAP7 on Steroid Biosynthesis in MA-10 Cell

Figure 6:
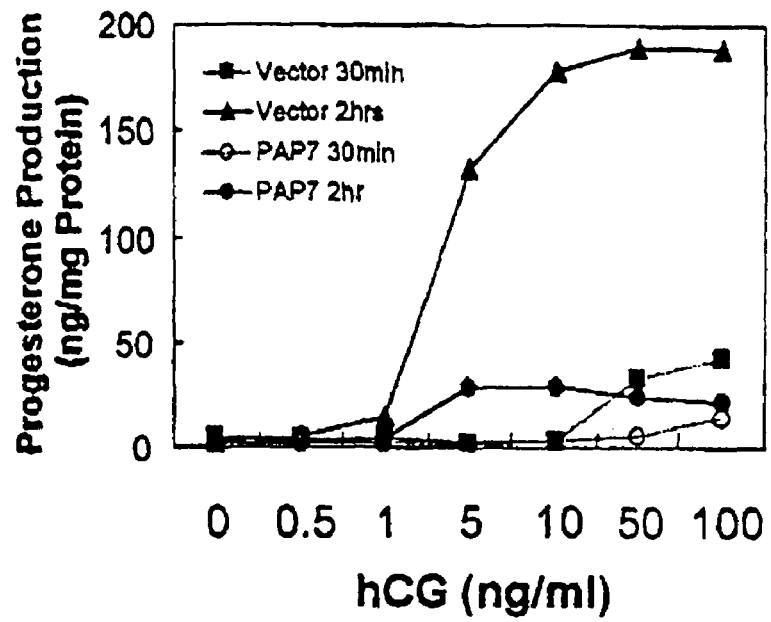
FIG. 6. The effect of PAP7 on Steroid Biosynthesis. Progesterone formation in MA-10 stimulated by hCG (A), for different time course (B). The results shown represent the means+S.D. from 2 to 6 independent experiments.
Figure 6:
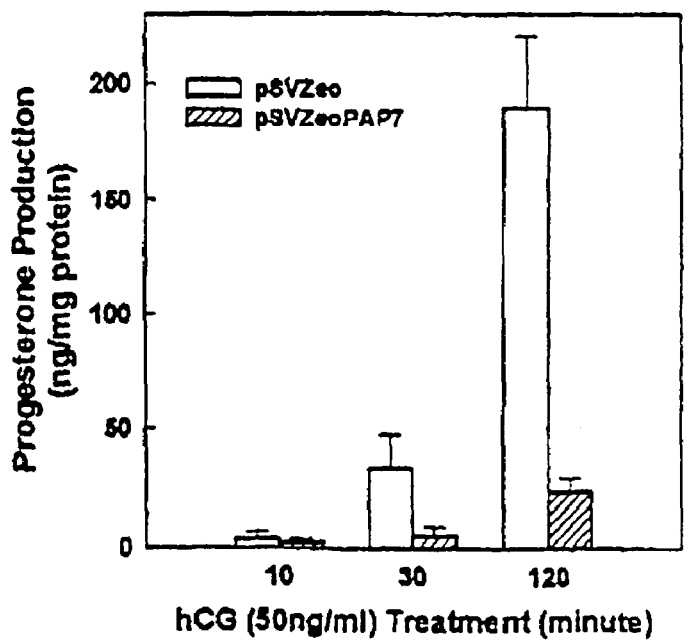

PAP7 partial sequence including PBR binding domain was subcloned into pSVzeo mammalian expression vector. This pSvzeoPAP7 vector was transiently transfected into MA-10 cells. pSVzeo empty vector was also transfected into cells as control. The capability of steroid biosynthesis of both empty vector pSVzeo transfectants and pSVzeoPAP7 transfectants was checked by monitoring the progesterone production in response to hormonal (hCG) stimulation. PAP7 transfectants had significantly reduced the level of progesterone production in MA-10 cells as compared with pSVzeo vector transfectant at a dose and time dependent manner (FIG. 6).

DISCUSSION

In order to better understand the mechanism of how PBR regulates cholesterol transport activity in steroid biosynthesis, we performed yeast two-hybrid assay to identify the PBR associated protein(s). Mouse PBR cDNA was inserted into the pGBT9 vector to generate a GAL4 DNA-binding domain and PBR fusion protein as bait. The receptor ligand binding activity of the fusion protein with PBR ligand, PK11195, was tested. Our result indicated that the fusion PBR protein expressed in yeast possessed the similar binding affinity as the native PBR protein (data not shown). PBR has been identified in various peripheral tissues (Gavish, M. and Weizman, R., 1997, *Clin. Neuropharmacol.* 20, 473–481) including testis. Testis is one of the important and very well studied tissues for steroidogenesis (Huhtaniemi, I, and Toppari, J., 1995, *Adv. Exp. Med. Biol.* 377, 33–54). The steroid biosynthesis in the mouse testicular Leydig cell and the role of PBR in this process are also well documented (Papadopoulos, V. et al., 1997, *Steroids* 62, 21–28; Papadopoulos, V. et al., 1998, *Endocr. Res.* 24, 479–487). Therefore, we applied mouse testis cDNA library in this two-hybrid screen study. The pGAD10 vector was used to generate a fusion protein of the GAL4 activation domain with a collection of random proteins in the fusion Balb/c mouse testis library. Through the yeast two hybrid screen, PAP7 was identified as one of the positive clones, which demonstrated its ability to interact with PBR (Table 1). Thus, we cloned the PAP7 cDNA coding for a mouse protein that interacted with PBR. Based on the database search, PAP7 is a novel gene product. Recently, PRAX-1 was reported as a new protein that specifically interates with PBR (Galiegue, S. et al., 1999, *J. Biol. Chem.* 274,2938–2952). The only similarity is that both proteins contain glutamic-acid streches. Part of PAP7 shares quite high homology with a *C. elegans* gene that has an unknown function (Wilson, R. et al., 1994, *Nature* 368, 32–38). In fact, cholesterol is required for *C. elegans* cell culture (Brenner, S., 1974, *Genetics* 77, 71–94). Considering that PBR is involved in cholesterol transport and PBR gene is highly conservative in all type of organisms, this data suggests that PAP7 expression may be needed to meet basic requirements for cell survival and growth. PAP7 also shares some homologies with RALBP, a hydrophobic ligand-binding protein that functions in intracellular retinoid transport (Ozaki, K. et al., 1994, *J. Biol. Chem.* 269, 3838–3845).

By sequence motif analysis using Swiss-Port Prosite profile scan, PAP7 has fatty acylation (myristoylation) sites, Acyl-CoA-binding protein signature and PKC phosphorylation sites. Protein myristoylation enables protein to attach to the cellular membrane and thus take part in cell signaling (Casey, P. J., 1995, Science 268, 221–225; Boutin, J. A., 1997, *Cell Signal* 9, 15–35). PBR is a hydrophobic protein and tightly associated with the outer mitochondrial membrane. This property could enable PAP7 passing hormone stimulation signal to and interacting with PBR thus regulating PBR activity in cholesterol transport. Interestingly, Acyl-CoA-binding protein is the other name of PBR endogenous ligand, diazepam binding inhibitor (DBI)(Rose, T. M. et al., 1992, *Proc. Natl. Acad. Sci. U.S.A.* 89, 11287–11291; Costa, E. and Guidotti, A., 1991, Life Sci. 49, 325–344; Suk, K. et al., 1999, *Biochim. Biophys. Acta* 1454, 126–131). This information suggests that PAP7 may coordinate with other PBR endogenous ligands to fulfill its function. The fact that PAP7 has the potential protein kinase phosphorylation sites raises another possibility that PBR could be regulated by hormone stimulation through the interaction with PAP7 protein.

The distribution and expression of PAP7 were examined in major mouse tissues such as brain, testis, ovary, adrenal, and kidney, as well as some cell lines. The PAP7 expressing pattern is similar to the broader expression profile of PBR. According to the previous studies (Papadopoulos, V. et al., 1998, supra), glucocorticoids are produced by zona fasciculata cells in adrenal. In the ovary, coupus luteum, where the granulosa cells are located, secretes progesterone. In addition, the testicular Leydig cells are able to produce testosterone. Since PAP7 is highly expressed in major steroidogenic tissues and is more concentrated in these steroid producing cells, PAP7 may be involved in steroid biosynthesis or the regulation of steroid formation by changing the formation or the conformation of the PBR complex. Mouse C6 glioma cells, MA-10 Leydig cells and Y1 adrenal cortical cells are popular cell models selected for studying steroid biosynthesis. PAP7 expression is proportionally correlated to the PBR expression in these cell lines. Additionally, both PBR and PAP7 expression level in these cell lines are parallel with their steroidogenic capability, which also suggests that PAP7 may be involved in steroid biosynthesis through a PBR pathway. A small PAP7 transcript was expressed only in testis, a phenomenon observed for other genes expressed in testis (Zhang, F. P. et al., 1997, Endocrinology 138, 2481–2490; Mauduit, C. et al., 1999, *J. Biol. Chem.* 274, 770–775). The immunostaining in the testis other than in Leydig cells could represent the expression of the smaller transcript.

The PAP7 protein is expressed in MA-10 cells and most of the staining is localized in the cytoplasm. The study of PAP7 subcellular distribution is ongoing, the results of which may provide more detailed information about the interaction between PBR and PAP7. Since PBR knockout mice die in uterus indicates an essential role for PBR essential in mouse embryonic development. Interestingly, PAP7 mRNA is highly expressed during mouse early embryonic development. This result may suggest that PAP7, associated with PBR, could play an important role during early mouse development. This further implies that PBR may have new functions beyond steroidogenesis. Overexpression of PAP7 fragment including its PBR binding domain significantly inhibited the progesterone formation stimulated by saturating concentrations of hCG (50 ng/ml) in MA-10 cells. According to previous studies, progesterone production of these cells represented the index of steroid biosynthesis (Freeman, D. A., 1987, *Endocrinology* 120, 124–132; Garnier, M. et al., 1994, *J. Biol. Chem.* 269, 22105–22112). Based on the inhibitory manner, we assume that the overexpressed PAP7 fragment might act as a competitor of the native PAP7 in MA-10 cells and competitively bind to PBR. We believe that the tranfected PAP7 fragment having Only the PBR binding domain and is not fully functional as a native PAP7, however, it competitively prevents PBR from interacting with the endogenous PAP7 and thereby blocks the normal function of PBR.

In conclusion, the results presented herein suggest that the identified PAP7 is involved in the regulation of the PBR function, serving as an endogenous ligand or allosteric modulator of the receptor.

Considering the findings tha i) PBR is a channel/transporter of cholesterol, ii) PBR is the target of environmental antisteroidogenic hazards, and (iii) PBR is involved in breast cancer aggression and tumor cell proliferation (Hardwick, M. et al., 1999, *Cancer Res.* 59, 831–842), we believe that the identification and characterization of PAP7 will greatly contribute to the understanding of the role of PBR in steroidogenesis and even in more general areas.

What is claimed is:

1. An isolated nucleic acid comprising a nucleotide sequence selected from the group consisting of:
   (a) a nucleotide sequence as set forth in SEQ ID NO: 2;
   (b) a nucleotide sequence encoding the polypeptide as set forth in SEQ ID NO: 7;
   (c) a nucleotide sequence complementary to (a) or (b).
2. A vector comprising the nucleic acid of claim 1.
3. The vector of claim 2, wherein said vector is an expression vector.
4. The vector of claim 2 that is a prokaryotic vector.
5. The vector of claim 2 that is a eukaryotic vector.
6. A host cell comprising the vector of claim 2.
7. A host cell of claim 6 that is a prokaryotic cell.
8. A host cell of claim 6 that is a eukaryotic cell.
9. A process of producing a peripheral-type benzodiazepine-associated protein (PAP) comprising culturing the host cell of either claim 7 or 8 under suitable conditions to express a peripheral-type benzodiazepine-associated protein-7 (PAP7) encoded by the nucleic acid.
10. The process of claim 9, wherein the vector further comprises a heterologous promoter operatively linked to the nucleotide sequence encoding the peripheral-type benzodiazepine-associated protein-7 (PAP7) polypeptide.
11. A reagent comprising a nucleic acid of claim 1, wherein the nucleic acid is detectably labeled.
12. A reagent comprising a single-stranded nucleic acid of claim 1, wherein the nucleic acid is complementary and is detectably labeled.
13. A reagent comprising a single-stranded nucleic acid of claim 1, wherein the nucleic acid amplifies peripheral-type benzodiazepine-receptor-associated protein-7 (PAP7) sequences.

* * * * *

UNITED STATES PATENT AND TRADEMARK OFFICE
CERTIFICATE OF CORRECTION

PATENT NO. : 7,056,694 B1
APPLICATION NO. : 09/762594
DATED : June 6, 2006
INVENTOR(S) : Papadopoulos et al.

It is certified that error appears in the above-identified patent and that said Letters Patent is hereby corrected as shown below:

On the face page, in field (54), in "Title", in column 1, line 2, delete "BENZODIAZIPINE" and insert --BENZODIAZEPINE --, therefor.

On the face page, in field (73), in "Assignee", in column 1, lines 1-2, delete "Washington, DC" and insert -- Washington D.C. --, therefor.

On the face page, in field (56), under "Foreign Patent Documents", in column 1, line 1, after "9/1999" insert -- G01N 33/574 --.

On the face page, in field (56), under "Foreign Patent Documents", in column 1, line 2, after "1/2000" insert -- C12N 15/12 --.

On the face page, in field (56), under "Foreign Patent Documents", in column 1, line 3, after "2/2000" insert -- C07K 14/00 --.

On the face page, in field (56), under "Other Publications", in column 2, line 6, delete "steroidogenesis," and insert -- steroidogenesis. --, therefor.

On the face page, in field (56), under "Other Publications", in column 2, line 12, delete "e tal." and insert -- et al. --, therefor.

On the face page, in field (56), under "Other Publications", in column 2, lines 39-43, below "1999.*" delete "Smith et al. The challenges of genome sequence annotation or "The devil is in the details". Nature Biotech 15: 1222-1223, 1997.*
Brenner, S.E. Errors in genome function. Trends in Genetics 15(4):132-133, 1999.*". (Entries repeated)

On page 2, in field (56), under "Other Publications", in column 1, line 3, delete "Wells." and insert -- Wells, --, therefor.

On page 2, in field (56), under "Other Publications", in column 1, line 27, delete "megi"," and insert -- megl", --, therefor.

On page 2, in field (56), under "Other Publications", in column 1, line 55, delete "Mitochrondrial" and insert -- Mitochondrial --, therefor.

On page 2, in field (56), under "Other Publications", in column 1, line 67, delete "26912695." and insert -- 2691-2695. --, therefor.

UNITED STATES PATENT AND TRADEMARK OFFICE
CERTIFICATE OF CORRECTION

PATENT NO. : 7,056,694 B1
APPLICATION NO. : 09/762594
DATED : June 6, 2006
INVENTOR(S) : Papadopoulos et al.

It is certified that error appears in the above-identified patent and that said Letters Patent is hereby corrected as shown below:

On page 2, in field (56), under "Other Publications", in column 2, line 1, delete ""Protentiation" and insert -- "Potentiation --, therefor.

On page 2, in field (56), under "Other Publications", in column 2, line 13, delete "Laborary" and insert -- Laboratory --, therefor.

On page 2, in field (56), under "Other Publications", in column 2, line 14, delete "2d" and insert -- 2nd --, therefor.

On page 2, in field (56), under "Other Publications", in column 2, line 14, delete "(1989)9." and insert -- (1989),9. --, therefor.

On page 2, in field (56), under "Other Publications", in column 2, line 16, after "H.," insert -- et al., --.

On page 2, in field (56), under "Other Publications", in column 2, line 19, delete "A-1.","" and insert -- A-I.", --, therefor.

On page 2, in field (56), under "Other Publications", in column 2, line 28, after "J." insert -- , --.

On page 2, in field (56), under "Other Publications", in column 2, line 52, delete Pubmed." and insert -- Pubmed, --, therefor.

On page 2, in field (56), under "Other Publications", in column 2, line 59, delete "cholestrol" and insert -- cholesterol --, therefor.

In column 1, line 2, delete "BENZODIAZIPINE" and insert -- BENZODIAZEPINE --, therefor.

In column 3, line 57, after "(SEQ ID NO:2)" insert -- , --.

In column 5, line 30, after "(A)" insert -- , --.

In column 5, line 55, delete "cells." and insert -- cells, --, therefor.

In column 5, line 62, delete "(B)." and insert -- (B), --, therefor.

UNITED STATES PATENT AND TRADEMARK OFFICE
CERTIFICATE OF CORRECTION

PATENT NO. : 7,056,694 B1
APPLICATION NO. : 09/762594
DATED : June 6, 2006
INVENTOR(S) : Papadopoulos et al.

It is certified that error appears in the above-identified patent and that said Letters Patent is hereby corrected as shown below:

In column 6, line 56, delete "(lacz" and insert -- (lacZ --, therefor.

In column 9, line 44, delete "acitivity" and insert -- activity --, therefor.

In column 10, line 5, delete "referece" and insert -- reference --, therefor.

In column 10, line 22, after "also" delete ",".

In column 12, line 17, delete "preferrably," and insert -- preferably, --, therefor.

In column 12, line 67, delete "transciption" and insert -- transcription --, therefor.

In column 13, lines 14-15, delete "underexpressin" and insert -- underexpressing --, therefor.

In column 14, line 8, delete "14C," and insert -- $^{14}$C, --, therefor.

In column 14, line 9, delete "$^{211}$A," and insert -- $^{211}$At, --, therefor.

In column 14, line 28, delete "latter" and insert -- letter --, therefor.

In column 14, line 36, after "and" delete "=".

In column 14, line 67, after "Biology" delete "." and insert -- , --, therefor.

In column 16, line 21, delete "substaially" and insert -- substantially --, therefor.

In column 16, line 28, delete "(4,4, diisothiocyanostilbene-" and insert -- (4,4'diisothiocyanostilbene- --, therefor.

In column 16, line 67, delete "antagonists" and insert -- antogonists --, therefor.

In column 17, line 43, delete "defficient" and insert -- deficient --, therefor.

In column 18, lines 57-58, delete "The following Materials and Methods were used in the Examples described below" and insert the same on line 59 as a new paragraph.

In column 18, line 58, delete "desribed" and insert -- described --, therefor.

UNITED STATES PATENT AND TRADEMARK OFFICE
CERTIFICATE OF CORRECTION

| | | |
|---|---|---|
| PATENT NO. | : 7,056,694 B1 | |
| APPLICATION NO. | : 09/762594 | |
| DATED | : June 6, 2006 | |
| INVENTOR(S) | : Papadopoulos et al. | |

It is certified that error appears in the above-identified patent and that said Letters Patent is hereby corrected as shown below:

In column 18, line 63, delete "actifity," and insert -- activity, --, therefor.

In column 18, line 64, delete "N-3H]" and insert -- N-$^3$H] --, therefor.

In column 19, line 7, after "from" delete "from". (Second Occurrence)

In column 19, lines 59-60, delete "Unviersity)." and insert -- University). --, therefor.

In column 20, line 1, delete "repectively," and insert -- respectively, --, therefor.

In column 20, line 47, after "PAP7" delete "-".

In column 21, line 40, delete "ans" and insert -- and --, therefor.

In column 21, lines 63-67, delete "Library plasmids from these transformants were rescued in E. coli strain DH5*a*. Both the His+ phenotype and the expression of *β*-galactosidase were confirmed by a second-round transformation of strain HF7c carrying pGBT9-PBR (Table 1)." and insert the same on line 62 (Approx.).

In column 22, line 42, delete "bot" and insert -- blot --, therefor.

In column 23, line 6, after "shown)" insert -- . --.

In column 23, line 59, delete "interates" and insert -- interacts --, therefor.

In column 25, line 12, delete "tranfected" and insert -- transfected --, therefor.

In column 25, line 13, delete "Only" and insert -- only --, therefor.

UNITED STATES PATENT AND TRADEMARK OFFICE
CERTIFICATE OF CORRECTION

PATENT NO.       : 7,056,694 B1
APPLICATION NO.  : 09/762594
DATED            : June 6, 2006
INVENTOR(S)      : Papadopoulos et al.

It is certified that error appears in the above-identified patent and that said Letters Patent is hereby corrected as shown below:

In column 26, line 7, delete "tha" and insert -- that --, therefor.

Signed and Sealed this

Thirtieth Day of January, 2007

JON W. DUDAS
*Director of the United States Patent and Trademark Office*